United States Patent

Sato et al.

Patent Number: 5,639,899
Date of Patent: Jun. 17, 1997

[54] PROSTAGLANDIN $E_1$ ANALOGUES

[75] Inventors: Fumie Sato, 1-219, Kugenumahigashi 3-Chome, Fujisawa-shi, Kanagawa 251; Takehiro Amano, Urawa; Kazuya Kameo, Kounosu; Tohru Tanami, Tokyo; Masaru Mutoh, Ohmiya; Naoya Ono, Tokyo; Jun Goto, Ohmiya, all of Japan

[73] Assignees: Taisho Pharmaceutical Co., Ltd.; Fumie Sato, both of Japan

[21] Appl. No.: 133,171

[22] PCT Filed: Apr. 21, 1992

[86] PCT No.: PCT/JP92/00513

§ 371 Date: Oct. 19, 1993

§ 102(e) Date: Oct. 19, 1993

[87] PCT Pub. No.: WO92/18472

PCT Pub. Date: Oct. 29, 1992

[30] Foreign Application Priority Data

Apr. 22, 1991 [JP] Japan ................ 3-182112
Aug. 27, 1991 [JP] Japan ................ 3-296739

[51] Int. Cl.⁶ .................................... C07C 59/00
[52] U.S. Cl. .................. 554/117; 554/213; 554/214; 554/221; 554/222; 560/121; 562/503
[58] Field of Search .................. 560/121, 122; 554/117; 584/213, 214, 221, 222; 562/503

[56] References Cited

U.S. PATENT DOCUMENTS

| | | | |
|---|---|---|---|
| 4,018,803 | 4/1977 | Smith | 260/408 |
| 4,029,681 | 6/1977 | Smith | 260/408 |
| 4,086,258 | 4/1978 | Smith | 260/408 |
| 4,104,474 | 8/1978 | Smith | 560/53 |
| 4,113,961 | 9/1978 | Smith | 560/53 |
| 4,113,962 | 9/1978 | Smith | 560/53 |
| 4,113,963 | 9/1978 | Smith | 560/53 |
| 4,113,964 | 9/1978 | Smith | 560/55 |
| 4,113,965 | 9/1978 | Smith | 560/61 |
| 4,113,966 | 9/1978 | Smith | 560/61 |
| 4,115,651 | 9/1978 | Smith | 560/55 |
| 4,117,233 | 9/1978 | Smith | 560/55 |
| 4,121,038 | 10/1978 | Smith | 560/53 |
| 4,124,616 | 11/1978 | Smith | 260/408 |
| 4,124,769 | 11/1978 | Smith | 560/121 |
| 4,125,734 | 11/1978 | Smith | 560/121 |
| 4,126,753 | 11/1978 | Smith | 560/121 |
| 4,130,718 | 12/1978 | Smith | 560/53 |
| 4,137,247 | 1/1979 | Smith | 260/408 |
| 4,205,179 | 5/1980 | Bundy | 560/121 |
| 4,229,585 | 10/1980 | Pellegata et al. | 560/55 |
| 4,325,970 | 4/1982 | Holland et al. | 424/311 |
| 4,489,092 | 12/1984 | Vorbruggen et al. | 560/121 |

FOREIGN PATENT DOCUMENTS

| | | |
|---|---|---|
| 14445 | 2/1974 | Japan . |
| 100445 | 8/1977 | Japan . |
| 100446 | 8/1977 | Japan . |
| 100447 | 8/1977 | Japan . |
| 100448 | 8/1977 | Japan . |
| 100449 | 8/1977 | Japan . |
| 93956 | 6/1982 | Japan . |
| 144753 | 8/1984 | Japan . |
| 1409637 | 4/1973 | United Kingdom . |
| 9316041 | 8/1993 | WIPO . |

OTHER PUBLICATIONS

Tsuboi, et al, "Pharmacological Evaluation of OP1206, a Prostaglandin $E_1$ Derivative, as an Antianginal Agent," Arch. Int. Pharmacodyn., vol. 247, pp. 89–102 (1980).

Primary Examiner—Deborah D. Carr
Attorney, Agent, or Firm—Lorusso & Loud

[57] ABSTRACT

Object: To provide novel prostaglandin $E_1$ analogues which have more excellent pharmaceutical effects, longer duration of the effects and less side-effects than the prior art prostaglandin $E_1$'s.

Constitution: A $PGE_1$ analogue represented by the formula:

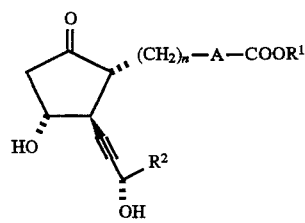

(wherein A is a vinylene group or an ethynylene group, $R^1$ is a hydrogen atom, an alkyl group having 1 to 6 carbon atoms or an allyl group, $R^2$ is a branched aliphatic hydrocarbon group having 5 to 10 carbon atoms), or a salt thereof.

16 Claims, No Drawings

PROSTAGLANDIN E₁ ANALOGUES

This application is a 371 of PCT/JP92/00513 filed Apr. 21, 1992, now WO 92-18472 published Oct. 29, 1992.

TECHNICAL FIELD

The present invention relates to novel prostaglandin (hereinafter referred to as PG) $E_1$ analogues.

BACKGROUND ART

Since PG's exhibit various important biological effects in a trace amount, investigations have been made of the synthesis and biological activity of natural PG's and a large number of PG analogues with the intention of use as medicines.

Especially, $PGE_1$ is now commercially available as a drug for the improvement of peripheral circulatory disturbances because of having characteristic effects such as blood platelet aggregation inhibiting effect and blood pressure reducing effect, and therefore, a large number of $PGE_1$ analogues have also been studied. However, the prior art $PGE_1$ analogues are quickly metabolized in vivo and thereby have drawbacks such as lack of duration of the effect. Furthermore, the prior art $PGE_1$ analogues cannot be administered orally in a sufficiently high amount to obtain the satisfactory effects because of causing diarrhea as a side-effect.

On the other hand, the known 13, 14-didehydro $PGE_1$ analogues in which the double bond between the 13- and 14-positions of $PGE_1$ is replaced by a triple bond include 13,14-didehydro $PGE_1$ methyl ester and 6-hydroxy-13,14-didehydro $PGE_1$.

An object of the present invention is to provide novel $PGE_1$ analogues which have more excellent pharmaceutical effects, longer duration of the effect and less side-effects than the prior art $PGE_1$ analogues.

DISCLOSURE OF THE INVENTION

As a result of continued extensive research, the present inventors have found that the compounds having a triple bond between the 13- and 14-positions of the $PGE_1$ analogues, a branch at the 16- or 17-position and a double or triple bond between the 2- and 3-positions can solve the above-mentioned problems, and have accomplished the present invention.

The present invention is directed to a $PGE_1$ analogue represented by the formula:

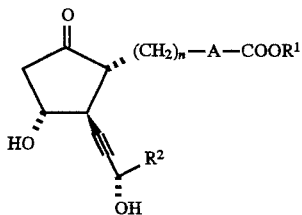

(I)

(wherein A is a vinylene group or an ethynylene group, $R^1$ is a hydrogen atom, an alkyl group having 1 to 6 carbon atoms or an allyl group, $R^2$ is a hydrocarbon group having 5 to 10 carbon atoms, and n is an integer of 3 to 6), or a salt thereof.

In the present invention, the alkyl group having 1 to 6 carbon atoms refers to a straight or branched chain alkyl group (e.g. a methyl group, an ethyl group, an n-propyl group, an isopropyl group, an n-butyl group, an isobutyl group, a t-butyl group, an n-pentyl group and an isopentyl group).

The hydrocarbon group having 5 to 10 carbon atoms refers to an hydrocarbon group having a branch at the α- or β-position, and particularly, a branched chain alkyl group (e.g. a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group and a 2,6-dimethylheptyl group), a cycloalkyl group (e.g. a cyclopentyl group, a cyclohexyl group and a cycloheptyl group), an alkyl group having 1 or 2 carbon atoms substituted by a cycloalkyl group (e.g. a cyclopentylmethyl group, a cyclohexylmethyl group, a cycloheptylmethyl group, a cyclopentylethyl group, a cyclohexylethyl group and a cycloheptylethyl group), a branched chain alkenyl group (e.g. a group which is obtained by converting a single bond at any position of the above-mentioned branched chain alkyl group into a double bond, such as a 2,6-dimethylhept-5-enyl group), a branched chain alkynyl group (e.g. a group which is obtained by converting a single bond at any position of the above-mentioned branched chain alkyl group into a triple bond, such as a 1-methylpent-3-ynyl group, a 1-methylhex-3-ynyl group and a 2-methylhex-3-ynyl group).

The salt of the compound of Formula (I) refers to salts thereof when $R^1$ is a hydrogen atom, for example, salts with metals (e.g. sodium, potassium and aluminium), or salts with organic amines (e.g. trialkylamine).

The compounds of Formula (I) can be prepared easily, for example, by the following processes.

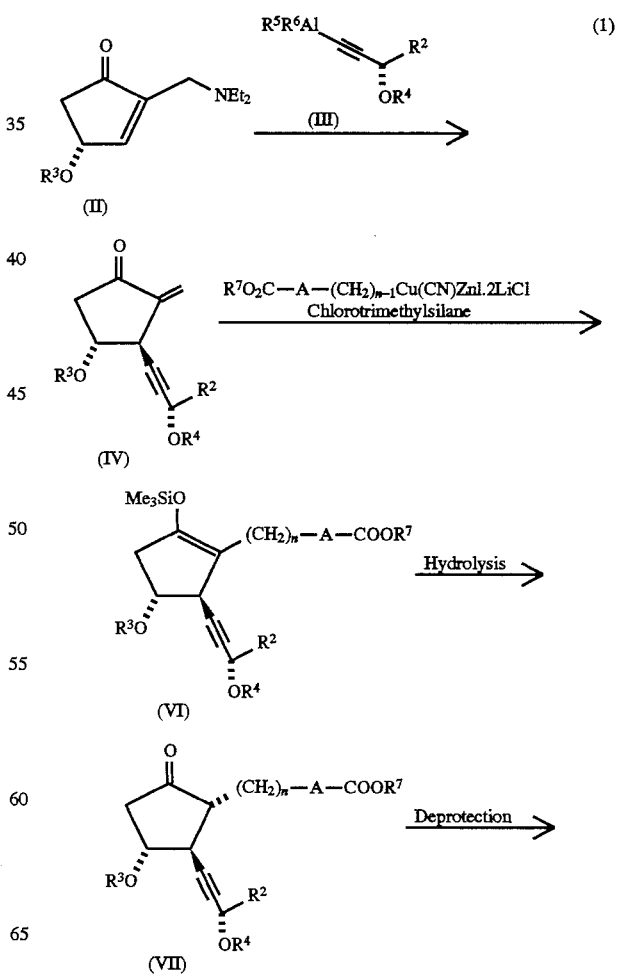

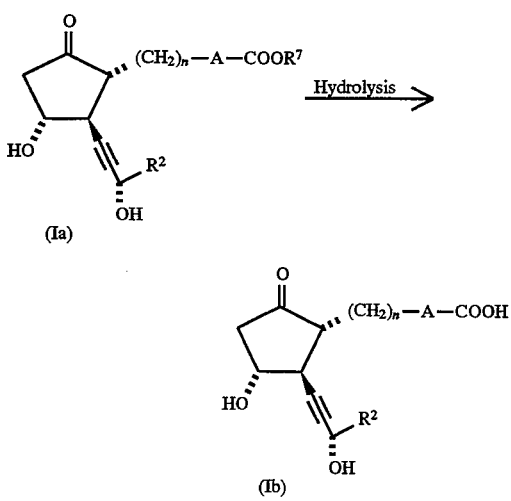

(wherein, $R^3$ and $R^4$ are the same or different, and are each a hydroxyl protecting group, $R^5$ and $R^6$ are the same or different, and are each an alkyl group having 1 to 10 carbon atoms, $R^7$ is the same as $R^1$ except a hydrogen atom, and $R^2$, A and n are as defined above. The hydroxyl protecting group refers to those usually used in the field of prostaglandins, such as a t-butyldimethylsilyl group, a triethylsilyl group, a phenyldimethylsilyl group, a tetrahydropyranyl group, a tetrahydrofuranyl group, a methoxymethyl group, an ethoxyethyl group and a benzyl group).

① First, the known compound of Formula (II) is reacted with 0.8 to 2.0 equivalents of an organic aluminium compound of Formula (III) in an inert solvent (e.g. benzene, toluene, tetrahydrofuran, diethyl ether, methylene chloride or n-hexane) at a temperature of −10° to 30° C., preferably 0° to 10° C., according to the method of Sato et al. [Journal of Organic Chemistry, vol. 53, page 5590 (1988)] to give a compound of Formula (IV) stereo-specifically.

The organic aluminium compound of Formula (III) can be prepared, for example, by completely achieving the reaction of an acetylene compound represented by the formula:

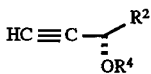

(wherein $R^2$ and $R^4$ are as defined above), which can be prepared according to the method of Sato et al. (Tetrahedron Letters, vol. 30, page 7083 (1989)], with 0.8 to 1.5 equivalents of an alkyllithium (e.g. n-butyllithium or t-butyllithium) at −20° to 30° C., preferably −10° to 0° C., more preferably 10° to 30° C., and then adding 0.8 to 1.5 equivalents of a halogenated alkylaluminium (e.g. diethylaluminium chloride or dimethylaluminium chloride) represented by the formula $$R^5R^6\text{—Al—X}$$

(wherein $R^5$ and $R^6$ are as defined above, and X is a halogen atom) at −20° to 30° C. In the reaction, it is preferable to use an inert organic solvent (e.g. benzene, toluene, tetrahydrofuran, diethyl ether, methylene chloride or n-hexane).

② Then, the compound of Formula (IV) is reacted with 0.5 to 4 equivalents of an organic copper compound of Formula (V) and 0.5 to 4 equivalents of chlorotrimethylsilane in an inert solvent (e.g. tetrahydrofuran, diethyl ether, methylene chloride, toluene or n-hexane) at −78° to 40° C. to give a compound of Formula (VI).

The organic copper compound of Formula (V) can be prepared from an iodide compound represented by the formula $$\text{I—(CH}_2)_{n-1}\text{—A—COOR}^7 \qquad (\text{VIII})$$

(wherein $R^7$, A and n are as defined above) according to the known method [P. Knochel et al;, Journal of Organic Chemistry, vol. 53, page 2390 (1988)]. That is, an iodide compound of Formula (VIII) is reacted with 0.8 to 5 equivalents of zinc activated, for example, by 1,2-dibromomethane, chlorotrimethylsilane or iodine in an inert solvent (e.g. tetrahydrofuran, diethyl ether, n-hexane, n-pentane or dioxane) to lead to an organic zinc compound represented by the formula:

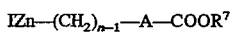

(wherein $R^7$, A and n are as defined above). In this case, the reaction, if desired, may be carried out with heating. The heating temperature, while dependant on the boiling point of the solvent to be used, is usually 30° to 150° C., preferably 40° to 80° C. The resulting organic zinc compound is reacted at −50° to 10° C. with copper cyanide (1 to 2.5 equivalents) in the same inert solvent as described above including lithium chloride (2 to 5 equivalents) to give an organic copper compound of Formula (V).

③ The compound of formula (VI) is hydrolyzed by using an inorganic acid (e.g. an aqueous hydrochloric acid solution) or an organic acid (e.g. p-toluenesulfonic acid) or an amine salt thereof (e.g. pyridinium p-toluenesulfonate) in an organic solvent (e.g. acetone, methanol, ethanol, isopropanol, diethyl ether or a mixture thereof) at 0° to 40° C. to stereoselectively give a compound of Formula (VII).

④ Finally, the hydroxyl protecting group of the compound of Formula (VII) is deprotected according to an ordinary method in the field of prostaglandins to give a compound of the present invention of Formula (I) wherein $R^1$ is other than a hydrogen atom (the compound of Formula (Ia)].

⑤ The present compound of Formula (I) wherein $R^1$ is a hydrogen atom [the compound of Formula (Ib)] can be prepared by hydrolyzing the ester moiety of the compound of Formula (Ia) wherein $R^7$ is an alkyl group having 1 to 6 carbon atoms [hereinafter referred to as compound of Formula (Ic)].

The hydrolysis is carried out by reacting the compound of Formula (Ic) with an enzyme in a buffer solution such as phosphate buffer or tris-hydrochloride buffer, if desired, by using an organic solvent (e.g. a water-miscible solvent such as acetone, methanol or ethanol).

Examples of the enzyme to be used are enzymes produced by microorganisms (e.g. enzymes produced by microorganisms belonging to *Candida* sp. and *Pseudomonas* sp.), and enzymes prepared from animal organs (e.g. pig liver and pig pancreas). Examples of the commercially available enzyme are lipase VII (produced by Sigma Co.; derived from microorganisms of *Candida* sp.), lipase AY (produced by Amano Pharmaceutical Co.; derived from microorganism of *Can-* dida sp.), lipase MF (produced by Amano Pharmaceutical Co.; derived from microorganism of *Pseudomonas* sp.), PLE-A (produced by Amano Pharmaceutical Co.; prepared from pig liver), esterase (produced by Sigma Co.; prepared from pig liver), lipbase II (produced by Sigma Co.; prepared from pig pancreas) and lipoprotein lipase (produced by Tokyo Kasei Kogyo Co.; prepared from pig pancreas).

The amount of the enzyme to be used, while dependant on the potency of the enzyme and the amount of the substrate [the compound of Formula (Ic)], is usually 0.1 to 20 times (by weight) relative to the substrate.

The reaction temperature is from 25° to 50° C., preferably 30° to 35° C.

(2) The compound of the present invention of Formula (I) wherein $R^1$ is a hydrogen atom can be also prepared from the compound of Formula (VII) wherein $R^7$ is an allyl group in the above item (1) according to the following process:

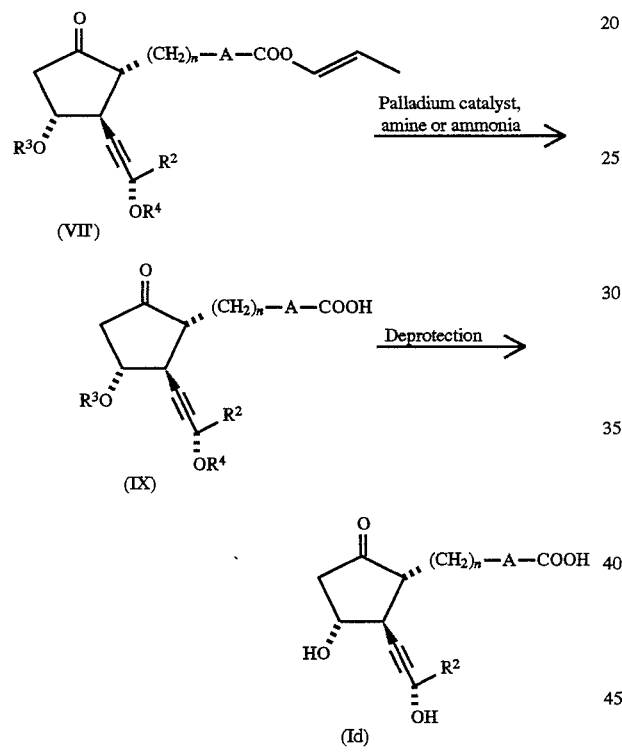

(wherein, $R^2$, $R^3$, $R^4$, A and n are as defined above).

① The compound of Formula (VII) wherein $R^7$ is an allyl group [the compound of Formula (VII')] in the above item (1) is first reacted with 1 to 10 equivalents of an organic amine or ammonia in the presence of a palladium catalyst to give a compound of Formula (IX).

Examples of the palladium catalyst are tris (dibenzylideneacetone)dipalladium(O)chloroform, bis (dibenzylideneacetone)palladium(O), tetrakis (triphenylphosphine)palladium(O), bis(acetylacetonate) palladium(II) and dichlorobis(benzonitrile)palladium (II). The amount of the palladium catalyst to be used is from 0.01 to 0.5 equivalent.

Examples of the organic amine are a primary or secondary organic amine such as, for example, ethylamine, diethylamine, morpholine and piperidine.

The reaction may be carried out, if necessary, in an inert organic solvent (e.g. diethyl ether or tetrahydrofuran). Also, it is preferable to add a phosphine (e.g. triethylphosphine, tributylphosphine and triphenylphosphine), unless phosphine forms a coordination compound with palladium as a catalyst.

② The hydroxyl protecting group of the compound of Formula (IX) is deprotected according to an ordinary method in the field of prostaglandins to give the compound of the present invention of Formula (I) wherein $R^1$ is a hydrogen atom [i.e. the compound of formula (Id)].

③ The compound of Formula (I) wherein A is a cis-vinylene group and $R^1$ is a hydrogen atom or an alkyl group having 1 to 6 carbon atoms can be also prepared from the compound of Formula (VII) wherein A is an ethynylene group in the above item (1) according to the following process.

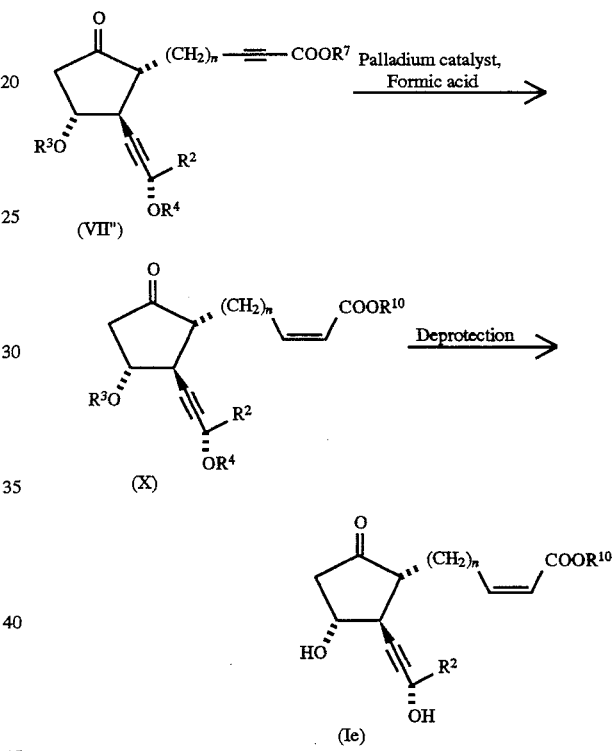

(wherein $R^2$, $R^3$, $R^4$, $R^7$ and n are as defined above, and $R^{10}$ is the same group as that of $R^7$ when $R^7$ is an alkyl group having 1 to 6 carbon atoms, or a hydrogen atom when $R^7$ is an allyl group).

① The compound of Formula (VII) wherein A is an ethynylene group [the compound of Formula (VII")] in the above item (1) is first reacted with 1 to 10 equivalents of formic acid in the presence of a palladium catalyst to give a compound of Formula (X).

The kind and amount of the palladium catalyst to be used herein are the same as described in the above item (2).

The reaction may be carried out, if necessary, in an inert organic solvent (e.g. diethyl ether or tetrahydrofuran) and a primary or secondary organic amine (i.e. ethylamine, diethylamine, morpholine or piperidine). Also, it is preferable to add a phosphine (e.g. triethylphosphine, tributylphosphine or triphenylphosphine), unless phosphine forms a coordination compound with palladium as a catalyst.

② The hydroxyl protecting group of the compound of Formula (X) is deprotected according to an ordinary method in the field of prostaglandins to give a compound of the present invention of Formula (I) wherein A is a cis-vinylene group, and $R^1$ is a hydrogen atom or an alkyl group having 1 to 6 carbon atoms [i.e. the compound of Formula (Ie)].

The compounds of the present invention can be administered orally or parenterally (e.g. intravenously, rectally or vaginally) in a dosage form such as solid forms (e.g. tablets, granules or capsules) and liquid forms (e.g. solutions, fat emulsions or liposome suspensions). For use of the oral dosage forms, the compounds of the present invention can be formulated into the form of the inclusion compounds with α-, β- or γ-cyclodextrin, or methylated cyclodextrin. Examples of the intravenous dosage forms are aqueous or non-aqueous solutions, emulsifiers, suspensions and solid formulations capable of dissolving in a solvent for injection immediately before use.

The rectal dosage forms include suppositories, and vaginal dosage forms include pessaries. The dose is from 0.1 to 100 μg, given in a single dose or up to 3 divided doses a day.

INDUSTRIAL UTILIZATION

It is apparent from the experiments described below that the compounds of the present invention have a potent blood platelet aggregation inhibiting effect and a long duration of such effect. Furthermore, the compounds of the present invention are useful as therapeutical drugs for various diseases including peripheral circulatory disturbances because they rarely induce diarrhea which is the largest problem caused by a dose of PG's exhibiting positive pharmaceutical effect.

The effects of the present invention are illustrated in more detail by the following experiments. Experiment 1 [Guinea-pig Blood Platelet Aggregation Inhibition Test]

supernatant. The remaining blood was further centrifuged at 1100×g for 10 minutes to give platelet poor plasma (PPP). The platelet count of PRP was adjusted to $4-6\times10^5/mm^3$ by using PPP. Blood platelet aggregation was determined according to the method of Born [Nature, vol. 194, page 927 (1962)]. That is, 275 μl of PRP was incubated with stirring at 1000 rpm at 37° C. for 3 minutes by using an aggrigometer, and then 25 μl of ADP (final concentration: 3 μM) or 25 μl of collagen (final concentration: 3 μg/ml) was added in order to induce blood platelet aggregation, and the maximum change of the light transmission obtained within 5 minutes was expressed as the maximum aggregation rate. From the following formula was calculated the aggregation inhibition rate of the group treated with the test drug to the maximum inhibition rate of the group treated with 0.5% carboxymethylcellulose solution as a control group.

$$\text{Aggregation inhibition rate (\%)} = \left(1 - \frac{\text{Maximum aggregation rate of group treated with test drug}}{\text{Maximum aggregation rate of control group}}\right) \times 100$$

Results are shown in Table 1. In the table are recited data of the compound obtained by converting the triple bond between the 13- and 14-positions of Compound 9 of Example 23 into a double bond as a comparative compound (limaprost) [Tsuboi et al, Arch. Intern. Pharmacodyn. Ther., vol. 247, page 89 (1980)].

In the experiment, the state of stool was observed for 2 hours after administration. As a result, significant diarrhea was found in the group treated with limaprost, and soft stool only was found in the group treated with the compounds of the present invention.

TABLE 1

| | Aggregation Inhibition Rate (%) | | | |
|---|---|---|---|---|
| | 2 hours after administration | | 8 hours after administration | |
| Test drug | ADP Aggregation | Collagen Aggregation | ADP Aggregation | Collagen Aggregation |
| Compound 1 | 9.8 | 25.7 | | |
| Compound 5 | 25.9 | 1.6 | | |
| Compound 6 | 22.8 | 58.2 | | |
| Compound 9 | 26.4 | 28.4 | | |
| Compound 14 | 52.5 | 100.0 | 31.8 | 61.0 |
| limaprost | 3.4 | 16.2 | | |

$p < 0.05$

Groups of five or six male Hartley strain guinea-pigs, each weighing 300 to 500 g, were used for the test after an overnight fast. A solution of the test drug in ethanol was suspended in 0.5% carboxymethyl-cellulose solution to give a final ethanol concentration of 1% or below. The test drug was orally administered in the amount of 50 μg/kg (5 cc of the solution per kg). Two or eight hours later, animals were anesthetized by abdominal administration of 20 mg/kg of pentobarbital. After laparotomy, blood was collected from the abdominal artery using a plastic syringe, and mixed with 3.2% sodium citrate in a volume ratio of 9:1. The blood was centrifuged at 120×g for 10 minutes to give PRP as a Experiment 2 [Rabbit Blood Platelet Aggregation Inhibition Test]

Groups of four New Zealand white strain rabbits, each weighing 2.5 to 4.0 kg, were used for the test. Blood was collected from the general carotid artery of the rabbits under an ether anesthesia, and mixed with 3.2% sodium citrate in a volume ratio of 9:1. The collected blood was Centrifuged at 1100 rpm for 15 minutes to give platelet rich plasma (PRP) as a supernatant. Blood platelet aggregation was determined according to the method of Born [Nature, vol. 194, page 927 (1962)]. That is, 1 μl of the test drug dissolved in ethanol at the desired concentration was added to 275 μl of PRP, and the mixture was stirred at 1000 rpm at 37° C. Three minutes later, 25 μl of an aggregation-inducing agent [adenosine diphosphate (ADP), final concentration: 5 μM] was added thereto, and the maximum aggregation rate (which is the maximum change of the light transmission obtained within 5 minutes) was determined by using an aggregometer.

The aggregation inhibition rate was calculated on the basis of the aggregation obtained by using ethanol in place of the test drug solution, and the aggregation inhibition activity was expressed as $IC_{50}$ value which was determined from the dose response curve.

Results are shown in Table 2 wherein the compound number is as defined in the examples described hereinafter, and the $IC_{50}$ value is expressed as the mean value.

TABLE 2

| Test drug | $IC_{50}$ value (nM) |
|---|---|
| Compound 2 | 1.7 |
| Compound 3 | 6.0 |
| Compound 4 | 3.0 |
| Compound 5 | 1.4 |
| Compound 7 | 1.1 |
| Compound 8 | 0.74 |
| Compound 9 | 2.6 |
| Compound 10 | 1.1 |
| Compound 11 | 6.3 |
| Compound 12 | 5.1 |
| Compound 13 | 2.7 |
| Compound 14 | 1.3 |
| Compound 15 | 5.1 |
| Compound 16 | 0.37 |
| limaprost | 6.3 |
| $PGE_1$ | 26 |

Experiment 3 [Human Blood Platelet Aggregation Inhibition Test]

Blood was collected from human, and immediately mixed with 3.8% aqueous sodium citrate solution in a volume ratio of 10:1. The blood was centrifuged at 180×g at room temperature for 15 minutes to give PRP as a supernatant. Blood platelet aggregation was determined according to the method of Born [Nature, vol. 194, page 927 (1962)]. That is, 5 μl of the test drug solution at the desired concentration was added to 100 μl of PRP, and the mixture was incubated with stirring at 1000 rpm at 37° C. for one minute by using an aggrigometer. Then, 5 μl of ADP was added thereto in order to induce blood platelet aggregation, and the maximum aggregation rate was determined.

The aggregation inhibition rate was calculated on the basis of the aggregation obtained by using saline solution in place of the test drug solution, $IC_{50}$ value was determined from the dose response curve, and the aggregation inhibition activity was expressed as the relative activity to $IC_{50}$ value of $PGE_1$ which was determined at the same time.

Results are shown in Table 3 wherein the compound number is as defined in the examples described hereinafter.

TABLE 3

| Test drug | Aggregation Inhibition Activity |
|---|---|
| $PGE_1$ | 1.00 |
| Compound 9 | 28.6 |
| Compound 10 | 103 |
| Compound 11 | 20.0 |

Experiment 4 [Blood Pressure Lowering Test in Anesthetized Dogs]

Male mongrel dogs, weighing 13 kg, were anesthetized by intravenous administration of 30 mg/kg of sodium pentobarbital. A cannula inserted into the left femoral vein was attached to a blood pressure transducer to measure blood pressure. A solution of the test drug in ethanol, if necessary, was diluted with ethanol. 10 μl of the solution was administered through the vein via a cannula inserted into the left anterior limb vein. The blood pressure lowering rate by the test drug was calculated by the following formula:

$$\text{Blood pressure lowering rate (\%)} = \left(1 - \frac{\text{Mean blood pressure before administration} - \text{Mean blood pressure at maximum response after administration}}{\text{Mean blood pressure before administration}}\right) \times 100$$

The blood pressure lowering rates of the compounds 1, 3 and 9 prepared in the examples hereinafter in the dose of 0.03 μg/kg were 10.1%, 11.5% and 23.7%, respectively. On the contrary, the blood pressure lowering rates of $PGE_1$ in the doses of 1 μg/kg and 3 μg/kg were 13.9% and 23.7%, respectively and those of limaprost in the doses of 0.5 μg/kg and 1 μg/kg were 13.9% and 23.8%, respectively.

BEST MODE OF CARRYING OUT THE INVENTION

The present invention is illustrated in more detail by the following examples.

(Note) In the nomenclature of the compounds, "nor" means lack of a carbon chain at the position (e.g. "17,18,19,20-tetranor" means lack of carbon atoms at the 17-, 18-, 19- and 20-positions), and "homo" means the increase of a carbon chain (e.g. "2a,2b-dihomo" means the increase of two carbon chains of 2a and 2b at the 2- and 3-positions).

The compounds prepared in the examples are listed in Table 4.

TABLE 4

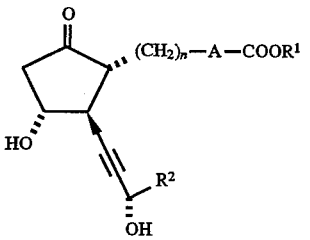

| Example number | R¹ | R² | A | n |
|---|---|---|---|---|
| 1 | methyl group | 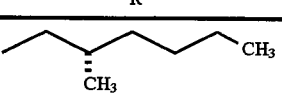 | t-vinylene group | 4 |
| 2 | methyl group | 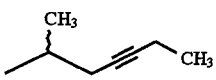 | t-vinylene group | 4 |
| 3 | methyl group | 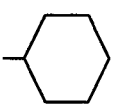 | t-vinylene group | 4 |
| 4 | methyl group | 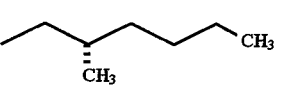 | ethynylene group | 4 |
| 5 | methyl group | 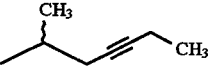 | ethynylene group | 4 |
| 6 | butyl group | 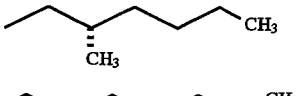 | t-vinylene group | 4 |
| 7 | methyl group | 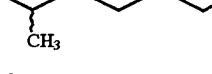 | t-vinylene group | 4 |
| 8 | methyl group | 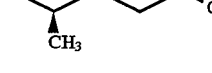 | t-vinylene group | 4 |
| 9 | methyl group | 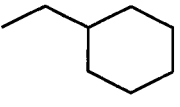 | t-vinylene group | 4 |
| 10 | methyl group | 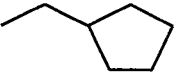 | t-vinylene group | 4 |
| 11 | methyl group | 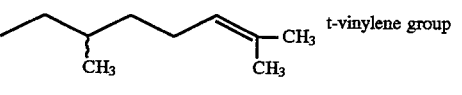 | t-vinylene group | 4 |
| 12 | butyl group | 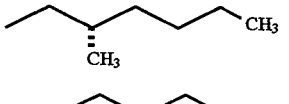 | ethynylene group | 4 |
| 13 | methyl group | 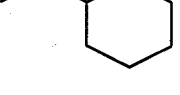 | ethynylene group | 4 |
| 14 | methyl group | 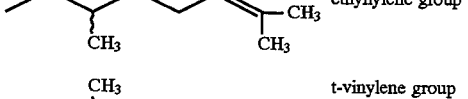 | ethynylene group | 4 |
| 15 | methyl group | 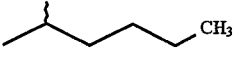 | t-vinylene group | 4 |

TABLE 4-continued

[Structure: cyclopentanone with (CH₂)ₙ—A—COOR¹ substituent, HO group, and alkyne-C(OH)(H)-R² side chain]

| Example number | R¹ | R² | A | n |
|---|---|---|---|---|
| 16 | methyl group | (H₃C)(CH₃)C-CH₂-CH₂-CH₂-CH₃ (neopentyl-type with gem-dimethyl) | t-vinylene group | 4 |
| 17 | methyl group | -CH₂-CH(CH₃)-CH₂-CH₂-CH₂-CH₃ | t-vinylene group | 5 |
| 18 | methyl group | -CH₂-CH(CH₃)-CH₂-CH₂-CH₂-CH₃ | t-vinylene group | 6 |
| 19 | methyl group | -CH₂-CH(CH₃)-CH₂-CH₂-CH₂-CH₃ | ethynylene group | 3 |
| 20 | methyl group | -CH₂-CH(CH₃)-CH₂-CH₂-CH₂-CH₃ | ethynylene group | 5 |
| 21 | allyl group | -CH₂-CH(CH₃)-CH₂-CH₂-CH₂-CH₃ | t-vinylene group | 4 |
| 22 | methyl group | -CH₂-CH(CH₃)-CH₂-CH₂-CH₂-CH₃ | ethynylene group | 4 |
| 23 | hydrogen atom | -CH₂-CH(CH₃)-CH₂-CH₂-CH₂-CH₃ | t-vinylene group | 4 |
| 24 | hydrogen atom | (CH₃)₂CH-CH(CH₃)-C≡C-CH₃ | t-vinylene group | 4 |
| 25 | hydrogen atom | cyclohexyl | t-vinylene group | 4 |
| 26 | hydrogen atom | (CH₃)₂CH-CH(CH₃)-C≡C-CH₃ | ethynylene group | 4 |
| 27 | hydrogen atom | -CH₂-CH(CH₃)-CH₂-CH₂-CH₂-CH₃ | ethynylene group | 4 |
| 28 | hydrogen atom | -CH₂-CH(CH₃)-CH₂-CH₂-CH₂-CH₂-CH₃ | t-vinylene group | 4 |
| 29 | hydrogen atom | -CH₂-CH(CH₃)-CH₂-CH₂-CH₂-CH₃ | t-vinylene group | 4 |
| 30 | hydrogen atom | cyclohexylmethyl | t-vinylene group | 4 |

TABLE 4-continued $$\text{structure: cyclopentanone with } (CH_2)_n\text{—A—COOR}^1 \text{ substituent, HO group, and alkyne-C(OH)R}^2 \text{ substituent}$$

| Example number | R¹ | R² | A | n |
|---|---|---|---|---|
| 31 | hydrogen atom | -CH₂-cyclopentyl | t-vinylene group | 4 |
| 32 | hydrogen atom | -CH₂-CH(CH₃)-CH₂-CH₂-CH=C(CH₃)₂ | t-vinylene group | 4 |
| 33 | hydrogen atom | -CH₂-CH(CH₃)-CH₂-CH₂-CH₃ | t-vinylene group | 4 |
| 34 | hydrogen atom | -CH₂-C(CH₃)₂-CH₂-CH₂-CH₃ | t-vinylene group | 4 |
| 35 | hydrogen atom | -CH₂-CH(CH₃)-CH₂-CH₂-CH₃ (≡) | t-vinylene group | 5 |
| 36 | hydrogen atom | -CH₂-CH(CH₃)-CH₂-CH₂-CH₃ (≡) | t-vinylene group | 6 |
| 37 | hydrogen atom | -CH₂-CH(CH₃)-CH₂-CH₂-CH₃ (≡) | ethynylene group | 3 |
| 38 | hydrogen atom | -CH₂-CH(CH₃)-CH₂-CH₂-CH₃ (≡) | ethynylene group | 5 |
| 39 | hydrogen atom | -CH₂-CH(CH₃)-CH₂-CH₂-CH₃ (▲) | ethynylene group | 4 |
| 40 | hydrogen atom | -CH₂-CH(CH₃)-CH₂-CH₂-CH₃ (▲) | t-vinylene group | 4 |
| 41 | hydrogen atom | -CH₂-CH(CH₃)-CH₂-CH₂-CH₃ (≡) | c-vinylene group | 4 |
| 42 | hydrogen atom | -CH₂-cyclopentyl | c-vinylene group | 4 |

(Note) In the table, "t-" and "c-" in "A" column mean trans- and cis-, respectively.

EXAMPLE 1

(2E,17S)-17,20-Dimethyl-2,3,13,14-tetradehydro-PGE₁ Methyl Ester (Compound 1)

(1) (3S,5S)-3-(t-Butyldimethylsiloxy)-5-methylnon-1-yne (3.85 g) was dissolved in 28.8 ml of benzene, and then n-butyl lithium (1.95M, hexane solution, 6.4 ml) was added thereto at 0° C., followed by stirring for 30 minutes at the same temperature. Diethylaluminium chloride (0.97M, hexane solution, 14.8 ml) was added at 0° C. to the solution, the temperature of which was allowed to rise to room temperature, followed by stirring for 30 minutes.

(4R)-2-(N,N-Diethylamino)methyl-4-(t-butyldimethylsiloxy)cyclopent-2-en-1-one (0.25M, benzene solution, 38.4 ml) was added at room temperature to the solution, followed by stirring for 15 minutes.

The reaction solution was poured into a mixture of hexane (100 ml), a saturated aqueous ammonium chloride solution (100 ml) and an aqueous hydrochloric acid solution (3M, 30 ml) with stirring, and the organic layer was collected and washed with a saturated aqueous sodium bicarbonate solution (50 ml). The resulting organic layer was dried and concentrated to give a residue, which was then purified by silica gel column chromatography (eluent; hexane:ether= 10:1) to give 3.72 g of (3R,4R)-2-methylene-3-[(3'S,5'S)-3'-(t-butyldimethylsiloxy)-5'-methylnon-1'-ynyl]-4-(t-butyldimethylsiloxy)cyclopentan-1-one.

$^1$H-NMR (CDCl$_3$, 300 MHz) δ ppm: 0.09, 0.10 and 0.12(3s, 12H), 0.89(s, 18H), 0.80~0.99(m, 6H), 1.00~1.72(m, 9H), 2.32(dd, J=7.4 Hz, 18.0 Hz, 1H), 2.71(dd, J=6.6 Hz, 18.0 Hz, 1H), 3.47~3.56(m, 1H), 4.15~4.33(m, 1H), 4.44(dt, J=1.6 Hz, 7.0 Hz, 1H), 5.54(d, J=2.6 Hz, 1H), 6.13(d, J=3.0 Hz, 1H)

IR(neat): 2930, 2850, 1740, 1640, 1460, 1360, 1250, 1120, 1080, 835, 770 cm$^{-1}$ (2) To (4E)-5-carbomethoxypent-4-enylzinc(II) iodide (0.64M tetrahydrofuran solution, 2.81 ml) was added at −70° C., a solution of copper (I) cyanide·dilithium dichloride (392 mg) in 2.25 ml of tetrahydrofuran, followed by stirring at the same temperature for 15 minutes. To the solution was added at −70° C., a solution of 434 mg of the compound obtained in the above item (1) and 0.21 ml of chlorotrimethylsilane in 3 ml of diethyl ether, followed by stirring to raise the temperature to room temperature over about a 2 hour period.

The reaction solution, after addition of 15 ml of a saturated aqueous ammonium chloride solution, was extracted with hexane. The organic layer was washed with a saturated aqueous sodium chloride solution, dried and concentrated to give a residue, which was then dissolved in 3.5 ml of ether—isopropyl alcohol (1:4). To the solution was added pyridinium p-toluenesulfonate (8.8 mg, 0.035 mmol), followed by stirring at room temperature for 12 hours.

To the reaction solution were added 20 ml of hexane and 10 ml of a saturated aqueous sodium bicarbonate solution, followed by extraction. The organic layer was dried and concentrated to give a residue, which was then chromatographed on silica gel column (eluent; hexane:ether=4:1) to give 532 mg of (2E, 17S)-17,20-dimethyl-2,3,13,14-tetradehydro-PGE$_1$ methyl ester 11,15-bis(t-butyldimethylsilyl ether).

$^1$H-NMR (CDCl$_3$, 300 MHz) δ ppm: 0.10(s, 6H), 0.11(s, 3H), 0.13(s, 3H), 0.83~0.98(m, 6H), 0.89(s, 9H), 0.90(s, 9H), 1.06~1.82(m, 15H), 2.11~2.29(m, 3H), 2.17(dd, J=7.0 Hz, 18.0 Hz, 1H), 2.59~2.77(m, 2H), 3.73(s, 3H), 4.23~4.35(m, 1H), 4.43(dt, J=1.5 Hz, 7.0 Hz, 1H), 5.82 (dt, J=1.5 Hz, 15.7 Hz, 1H), 6.96(dt, J=6.9 Hz, 15.7 Hz, 1H)

IR(neat): 2954, 2930, 2858, 2234, 1748, 1728, 1660, 1463, 1436, 1362, 1326, 1259, 1198, 1124, 1092, 1006, 838, 779, 670 cm$^{-1}$ (3) The compound (532 mg, 0.857 mmol) obtained in the above item (2) was dissolved in acetonitrile (29 ml), and then 50% aqueous hydrofluoric acid solution (6.9 ml) was added thereto at 0° C., followed by stirring at 0° C. for 90 minutes. The reaction solution was poured into ethyl acetate (40 ml) and a saturated aqueous sodium bicarbonate solution (230 ml). The mixture was extracted with ethyl acetate, washed with a saturated aqueous sodium bicarbonate solution and a saturated aqueous sodium chloride solution, dried and concentrated. The resulting residue was purified by silica gel column chromatography (eluent; ethyl acetate:methanol=40:1) to give 305 mg of the title compound.

$^1$H-NMR (CDCl$_3$, 300 MHz) δ ppm: 0.83~0.97(m, 6H), 1.08~1.90(m, 15H), 2.12~2.30(m, 4H), 2.62(dd, J=9.0 Hz, 10.5 Hz, 1H), 2.75(dd, J=7.3 Hz, 18.5 Hz, 1H), 2.92(br. s, 2H), 3.72(s, 3H), 4.27~4.36(m, 1H), 4.47(dt, J=1.0 Hz, 6.7 Hz, 1H), 5.68(d, J=15.7 Hz, 1H), 6.96(dt, J=7.4 Hz, 15.7 Hz, 1H)

IR(neat): 3380, 2910, 2230, 1720, 1700, 1650, 1435, 1270, 1040 cm$^{-1}$

EXAMPLE 2

(2E,16RS)-16,20-Dimethyl-2,3,13,14,18,18,19,19-octadehydro-PGE$_1$ Methyl Ester (Compound 2)

(1) Following a substantially similar manner to that of Example 1(1) but using (3S,4RS)-3-(t-butyldimethylsiloxy)-4-methylnona-1,6-diyne in place of (3S,5S)-3-(t-butyldimethylsiloxy)-5-methylnon-1-yne in Example 1(1), there was obtained (3R,4R)-2-methylene-3-[(3'S,4'RS)-3'-(t-butyldimethylsiloxy)-4'-methylnona-1',6'-diynyl]-4-(t-butyldimethylsiloxy)cyclopentan-1-one.

$^1$H-NMR(CDCl$_3$, 300 MHz) δ ppm: 0.09, 0.10 and 0.12(3s, 12H), 0.88(s, 18H), 1.02 and 1.03(2d, J=6.8 Hz and 6.8 Hz, 3H), 1.10(t, J=7.3 Hz, 3H), 1.73~1.91(m, 1H), 2.00~2.39(m, 4H), 2.32(dd, J=7.4 Hz, 17.9 Hz, 1H), 2.70(dd, J=6.4 Hz, 17.9 Hz, 1H), 3.53(d, J=6.5 Hz, 1H), 4.21~4.30(m, 1H), 4.37 and 4.47(2d, J=4.1 Hz, 6.3 Hz, 1H), 5.54(d, J=2.7 Hz, 1H), 6.13(d, J=3.0 Hz, 1H)

IR(neat): 2960, 2934, 2862, 2364, 1738, 1649, 1473, 1363, 1255, 1123, 1079, 837, 777 cm$^{-1}$ (2) Following similar manners to those of Examples (2) and (3) using the compound obtained in the above item (1), the title compound was obtained.

$^1$H-NMR (CDCl$_3$, 300 MHz) δ ppm: 0.90~1.16(m, 6H), 1.30~1.99(m, 7H), 2.04~2.37(m, 8H), 2.63(t, J=10.0 Hz, 1H), 2.75(dd, J=7.2 Hz, 18.5 Hz, 1H), 3.72(s, 3H), 4.27~4.38(m, 1H), 4.42 and 4.46(2d, J=6.6 Hz and J=4.4 Hz, 1H), 5.82(d, J=15.7 Hz, 1H), 6.95(dt, J=7.4 Hz, 15.7 Hz, 1H)

IR(neat): 3390, 2910, 2230, 1730, 1690, 1650, 1430, 1270, 1010 cm$^{-1}$

EXAMPLE 3

(2E)-16,17,18,19,20-Pentanor-15-cyclohexyl-2,3,13,14-tetradehydro-PGE$_1$ Methyl Ester (Compound 3)

(1) Following a substantially similar manner to that of Example 1(1) but using (3S)-3-(t-butyldimethylsiloxy)-3-cyclohexylprop-1-yne in place of (3S,5S)-3-(t-butyldimethylsiloxy)-5-methylnon-1-yne in Example 1(1), there was obtained (3R,4R)-2-methylene-3-[(3'S)-3'-(t-butyldimethylsiloxy)-3'-cyclohexylprop-1'-ynyl]-4-(t-butyldimethylsiloxy)cyclopentan-1one.

$^1$H-NMR(CDCl$_3$, 200 MHz) δ ppm: 0.07, 0.08 and 0.12(3s, 12H), 0.88(s, 18H), 0.92~1.92(m, 11H), 2.32(dd, J=7.4 Hz, 17.8 Hz, 1H), 2.71(dd, J=6.5 Hz, 17.8 Hz, 1H), 3.48~3.58(m, 1H), 4.11(dd, J=1.4 Hz, 6.2 Hz, 1H), 4.20~4.32(m, 1H), 5.55(d, J=2.6 Hz, 1H), 6.13(d, J=3.0 Hz, 1H)

IR(neat): 2930, 2850, 1735, 1640, 1470, 1380, 1255, 1105, 830, 770 cm$^{-1}$ (2) Following similar manners to those of Examples 1(2) and (3) using the compound obtained in the above item (1), the title compound was obtained.

$^1$H-NMR(CDCl$_3$, 300 MHz) δ ppm: 0.96~1.95(m, 17H), 2.12~2.40(m, 4H), 2.63(ddd, J=1.6 Hz, 8.4 Hz, 11.8 Hz, 1H), 2.76(dd, J=7.4 Hz, 18.5 Hz, 1H), 2.83(br. s, 2H), 3.73(s, 3H), 4.18(dd, J=1.6 Hz, 6.2 Hz, 1H), 4.27~4.38(m, 1H), 5.83(d, J=15.7 Hz, 1H), 6.96(dt, J=15.7, 7.0 Hz, 1H)

IR(neat): 3400, 2920, 2230, 1720, 1700, 1650, 1440, 1270, 1160 cm$^{-1}$

EXAMPLE 4

(71S)-17,20-Dimethyl-2,2,3,3,13,14-hexadehydro-PGE$_1$ Methyl Ester (Compound 4)

Following a substantially similar manner to that of Example 1 but using 5-carbomethoxypent-4-ynylzinc(II)

iodide in place of (4E)-5-carbomethoxypent-4-enylzinc(II) iodide in Example 1(2), the title compound was obtained.
$^1$H-NMR(CDCl$_3$, 300 MHz) δ ppm: 0.90(t, J=6.8 Hz, 3H), 0.92(d, J=6.4 Hz, 3H), 1.10~1.89(m, 15H), 2.18~2.31(m, 1H), 2.23(d, J=5.7 Hz, 1H), 2.24(dd, J=8.9 Hz, 18.6 Hz, 1H), 2.36(t, J=6.5 Hz, 2H), 2.66(ddd, J=1.8 Hz, 8.1 Hz, 11.2 Hz, 1H), 2.71(d, J=3.4 Hz, 1H), 2.76(ddd, J=1.3 Hz, 7.2 Hz, 18.6 Hz, 1H), 3.76(s, 3H), 4.28~4.38(m, 1H), 4.43~4.51(m, 1H)
IR(neat): 3402, 2930, 2861, 2237, 1746, 1718, 1436, 1259, 1152, 1078, 754 cm$^{-1}$

EXAMPLE 5

(16RS)-16,20-Dimethyl-2,2,3,3,13,14,18,18,19,19-decadehydro-PGE$_1$ Methyl Ester Following substantially similar manners to those of Examples 1(2) and (3) but using 5-carbomethoxypent-4-ynylzinc(II) iodide and the compound obtained in Example 1(1) in place of (4E)-5-carbomethoxypent-4-enylzinc(II) iodide in Example 1(2) and the compound obtained in Example 1(1) respectively, the title compound was obtained.
$^1$H-NMR(CDCl$_3$, 300 MHz) δ ppm: 1.05(d, J=6.7 Hz, 3H), 1.11(t, J=7.5 Hz, 3H), 1.79~1.90(m, 1H), 2.01~2.88(m, 15H), 2.92(br. s, 2H), 3.10(q, J=7.6 Hz, 1H), 3.71(s, 3H), 4.24~4.33(m, 1H), 4.32 and 4.38(2d, J=4.1 Hz and J=2.9 Hz, 1H)

EXAMPLE 6

(2E,17S)-17,20-Dimethyl-2,3,13,14-tetradehydro-PGE$_1$ n-butyl Ester

Following a substantially similar manner to that of Example 1 but using (4E)-5-carbobutoxypent-4-enylzinc(II) iodide in place of (4E)-5-carbomethoxypent-4-enylzinc(II) iodide in Example 1(2), the title compound was obtained.
$^1$H-NMR(CDCl$_3$, 300 MHz) δ ppm: 0.78~0.97(m, 9H), 1.09~1.86(m, 19H), 2.12~2.30(m, 4H), 2.55~2.68(m, 1H), 2.74(dd, J=7.2 Hz, 18.6 Hz, 1H), 4.12(t, J=6.6 Hz, 2H), 4.26~4.36(m, 1H), 4.46(t, J=6.9 Hz, 1H), 5.82(d, J=15.7 Hz, 1H), 6.94(dt, J=7.3 Hz, 15.7 Hz, 1H)
IR(neat): 3370, 2920, 2310, 1720, 1690, 1640, 1450, 1260, 1170, 1060 cm$^{-1}$

EXAMPLE 7

(2E,17RS)-17-Methyl-20-ethyl-2,3,13,14-tetradehydro-PGE$_1$ Methyl Ester (1) Following a substantially similar manner to that of Example 1(1) but using (3S,5RS)-3-(t-butyldimethylsiloxy)-5-methyldec-1-yne in place of (3S,5S)-3-(t-butyldimethylsiloxy)-5-methylnon-1-yne in Example 1(1), there was obtained (3R,4R)-2-methylene-3-[(3'S,5'RS)-3'-(t-butyldimethylsiloxy)-5'-methyldec-1'-ynyl]-4-(t-butyldimethylsiloxy)cyclopentan-1-one.
$^1$H-NMR(CDCl$_3$, 300 MHz) δ ppm: 0.10 and 0.13(2s, 12H), 0.80~1.05(m, 24H), 1.06~1.80(m, 11H), 2.33(dd, J=7.4 Hz, 18.1 Hz, 1H), 2.71(dd, J=6.3 Hz, 18.1 Hz, 1H), 3.43~3.66(m, 1H), 4.20~4.35(m, 1H), 4.45(t, J=6.5 Hz, 1H), 5.55(br. s, 1H), 6.14(br. s, 1H)
IR(neat): 2920, 2850, 2330, 1730, 1630, 1460, 1360, 1240, 1110, 1080, 830, 770 cm$^{-1}$ (2) Following similar manners to those of Examples 1(2) and (3) using the compound obtained in the above item (1), the title compound was obtained.
$^1$H-NMR(CDCl$_3$, 300 MHz) δ ppm: 0.70~0.92(m, 6H), 0.92~1.85(m, 17H), 1.85~2.33(m, 4H), 2.33~2.79(m, 1H), 2.73(dd, J=7.1 Hz, 18.4 Hz, 1H), 3.71(s, 3H), 4.15~4.49(m, 2H), 5.81(d, J=15.6 Hz, 1H), 6.92(dt, J=7.5 Hz, 15.6 Hz, 1H)
IR(neat): 3390, 2930, 2860, 2220, 1720, 1710, 1650, 1440, 1280, 1040 cm$^{-1}$

EXAMPLE 8

(2E,17R)-17,20-Dimethyl-2,3,13,14-tetradehydro-PGE$_1$ Methyl Ester (Compound 5)

(1) Following a substantially similar manner to that of Example 1(1) but using (3S,5R)-3-(t-butyldimethylsiloxy)-5-methylnon-1-yne in place of (3S,5S)-3-(t-butyldimethylsiloxy)-5-methylnon-1-yne in Example 1(1), there was obtained (3R,4R)-2-methylene-3-[(3'S,5'R)-3'-(t-butyldimethylsiloxy)-5'-methylnon-1'-ynyl]-4-(t-butyldimethylsiloxy)cyclopentan-1-one.
$^1$H-NMR(CDCl$_3$, 300 MHz) δ ppm: 0.03~0.15(m, 12H), 0.80~0.93(m, 24H), 1.06~1.80(m, 9H), 2.33(dd, J=7.4 Hz, 17.9 Hz, 1H), 2.71(dd, J=6.4 Hz, 17.9 Hz, 1H), 3.41~3.56(m, 1H), 4.20~4.32(m, 1H), 4.44(t, J=6.6 Hz, 1H), 5.55(br. s, 1H), 6.14(br. s, 1H)
IR(neat): 2920, 2850, 2210, 1730, 1630, 1450, 1360, 1240, 1100, 1080, 820, 760 cm$^{-1}$ (2) Following similar manners to those of Examples 1(2) and (3) using the compound obtained in the above item (1), the title compound was obtained.
$^1$H-NMR(CDCl$_3$, 300 MHa) δ ppm: 0.70~0.98(m, 6H), 1.05~1.90(m, 15H), 2.02~2.36(m, 4H), 2.55(br. s, 2H), 2.43~2.84(m, 1H), 2.77(dd, J=7.3 Hz, 18.6 Hz, 1H), 3.74(s, 3H), 4.28~4.56(m, 2H), 5.84(d, J=15.7 Hz, 1H), 6.99(dt, J=7.5 Hz, 15.7 Hz, 1H)
IR(neat): 3390, 2930, 2860, 2220, 1730, 1660, 1460, 1440, 1280, 1040 cm$^{-1}$

EXAMPLE 9

(2E)-17,18,19,20-Tetranor-16-cyclohexyl-2,3,13,14-tetradehydro-PGE$_1$ Methyl Ester (1) Following a substantially similar manner to that of Example 1(1) but using (3S)-3-(t-butyldimethylsiloxy)-4-cyclohexylbut-1-yne in place of (3S,5S)-3-(t-butyldimethylsiloxy)-5-methylnon-1-yne in Example 1(1), there was obtained (3R,4R)-2-methylene-3-[(3'S)-3'-(t-butyldimethylsiloxy)-4'-cyclohexylbut-1'-ynyl]-4-(t-butyldimethylsiloxy)cyclopentan-1-one.
$^1$H-NMR(CDCl$_3$, 300 MHz) δ ppm: 0.07~0.14(m, 12H), 0.89(s, 18H), 1.03~1.80(m, 13H), 2.33(dd, J=7.4 Hz, 17.9 Hz, 1H), 2.71(dd, J=6.4 Hz, 17.9 Hz, 1H), 3.41~3.54(m, 1H), 4.22~4.32(m, 1H), 4.47(t, J=6.8 Hz, 1H), 5.55(d, J=2.5 Hz, 1H), 6.14(d, J=2.7 Hz, 1H)
IR(neat): 2930, 2850, 1735, 1640, 1460, 1360, 1250, 1220, 1100, 1000, 940, 830, 770 cm$^{-1}$ (2) Following similar manners to those of Examples 1(2) and (3) using the compound obtained in the above item (1), the title compound was obtained.
$^1$H-NMR(CDCl$_3$, 300 MHz) δ ppm: 0.81~1.85(m, 19H), 2.10~2.42(m, 4H), 2.55~2.66(m, 1H), 2.73(dd, J=7.2 Hz, 18.4 Hz, 1H), 3.73(s, 3H), 4.29(q, J=8.5 Hz, 1H), 4.45(t, J=6.3 Hz, 1H), 5.80(d, J=15.7 Hz, 1H), 6.96(dt, J=7.0 Hz, 15.7 Hz, 1H)
IR(neat): 3400, 2920, 2850, 2320, 1720, 1700, 1650, 1440, 1270, 1200, 1160, 1035, 980 cm$^{-1}$

EXAMPLE 10

(2E)-17,18,19,20-Tetranor-16-cyclopentyl-2,3,13,14-tetradehydro-PGE$_1$ Methyl Ester (1) Following a substantially similar manner to that of Example 1(1) but using (3S)-3-(t-butyldimethylsiloxy)-4- cyclopentylbut-1-yne in place of (3S,5S)-3-(t-butyldimethylsiloxy)-5-methylnon-1-yne in Example 1(1), there was obtained (3R,4R)-2-methylene-3-[(3'S)-3'-(t-butyldimethylsiloxy)-4'-cyclopentylbut-1'-ynyl]-4-(t-butyldimethylsiloxy)cyclopentan-1-one.

$^1$H-NMR(CDCl$_3$, 300 MHz) δ ppm: 0.07~0.17(m, 12H), 0.89(s, 18H), 1.03~2.02(m, 11H), 2.33(dd, J=7.6 Hz, 17.9 Hz, 1H), 2.71(dd, J=6.4 Hz, 17.9 Hz, 1H), 3.41~3.58(m, 1H), 4.22~4.31(m, 1H), 4.39(t, J=6.7 Hz, 1H), 5.55(d, J=2.4 Hz, 1H), 6.14(d, J=3.0 Hz, 1H)

IR(neat): 2930, 2850, 1735, 1638, 1460, 1360, 1245, 1220, 1100, 1000, 935, 825, 770 cm$^{-1}$ (2) Following similar manners to those of Examples 1(2) and (3) using the compound obtained in the above item (1), the title compound was obtained.

$^1$H-NMR(CDCl$_3$, 300 MHz) δ ppm: 1.02~2.05(m, 17H), 2.13~2.31(m, 4H), 2.52~2.66(m, 1H), 2.74(dd, J=7.2 Hz, 18.7 Hz, 1H), 3.72(s, 3H), 4.25~4.43(m, 1H), 4.39(t, J=7.1 Hz, 1H), 5.81(d, J=15.7 Hz, 1H), 6.94(dt, J=6.9 Hz, 15.7 Hz, 1H)

IR(neat): 3380, 2920, 2855, 2240, 1715, 1650, 1440, 1270, 1160, 1035, 725 cm$^{-1}$

EXAMPLE 11

(2E,17RS)-20-Nor-17-methyl-19-(2'-methylprop-1'-enyl)-2,3,13,14-tetradehydro-PGE$_1$ Methyl Ester (1) Following a substantially similar manner as that of Example 1(1) but using (3S,5RS)-3-(t-butyldimethylsiloxy)-5,9-dimethyldec-8-en-1-yne in place of (3S,5S)-3-t-butyldimethylsiloxy)-5-methylnon-1-yne in Example 1(1), there was obtained (3R,4R)-2-methylene-3-[(3'S,5'RS)-3'-(t-butyldimethylsiloxy)-5',9'-dimethyldec-8'-en-1'-ynyl]-4-(t-butyldimethylsiloxy)cyclopentan-1-one.

$^1$H-NMR(CDCl$_3$, 300 MHz) δ ppm: 0.10 and 0.13(2s, 12H), 0.80~1.02(m, 21H), 1.05~1.82(m, 5H), 1.60(s, 3H), 1.67(s, 3H), 1.90~2.06(m, 2H), 2.33(dd, J=7.4 Hz, 17.8 Hz, 1H), 2.71(dd, J=6.4 Hz, 17.8 Hz, 1H), 3.49~3.57(m, 1H), 4.22~4.37(m, 1H), 4.45(t, J=5.9 Hz, 1H), 5.08(t, J=6.1 Hz, 1H), 5.55(d, J=1.8 Hz, 1H), 6.14(d, J=2.5 Hz, 1H)

(2) Following similar manners to those of Examples 1(2) and (3) using the compound obtained in the above item (1), the title compound was obtained.

$^1$H-NMR(CDCl$_3$, 300 MHz) δ ppm: 0.82~1.01(m, 3H), 1.10~2.35(m, 16H), 1.59(s, 3H), 1.67(s, 3H), 2.56~2.65(m, 2H), 2.74(dd, J=7.3 Hz, 18.5 Hz, 1H), 3.72(s, 3H), 4.25~4.36(m, 1H), 4.46(t, J=6.6 Hz, 1H), 5.08(t, J=5.7 Hz, 1H), 5.82(d, J=15.6 Hz, 1H), 6.95(dt, J=6.8 Hz, 15.6 Hz, 1H)

IR(neat): 3400, 2920, 2860, 2270, 1725, 1705, 1650, 1440, 1280, 1020 cm$^{-1}$

EXAMPLE 12

(17S)-17,20-Dimethyl-2,2,3,3,13,14-hexadehydro-PGE$_1$ n-butyl Ester (Compound 6)

Following a substantially similar manner to that of Example 1 but using 5-carbobutoxypent-4ynylzinc(II) iodide in place of (4E)-5-carbomethoxypent-4-enylzinc(II) iodide in Example 1(2), the title compound was obtained.

$^1$H-NMR(CDCl$_3$, 300 MHz) δ ppm: 0.78~0.98(m, 9H), 1.05~1.88(m, 19H), 2.16~2.42(m, 4H), 2.57~2.66(m, 1H), 2.74(dd, J=7.1 Hz, 18.5 Hz, 1H), 4.14(t, J=6.6 Hz, 2H), 4.25~4.37(m, 1H), 4.45(t, J=6.9 Hz, 1H)

IR(neat): 3400, 2940, 2240, 1740, 1700, 1460, 1250, 1070 cm$^{-1}$

EXAMPLE 13

17,18,19,20-Tetranor-16-cyclohexyl-2,2,3,3,13,14-hexadehydro-PGE$_1$ Methyl Ester Following substantially similar manners to those of Examples 1(2) and (3) but using 5-carbobutoxypent-4-ynylzinc(II) iodide and the compound obtained Example 9(1) in place of (4E)-5-carbomethoxypent-4-enylzinc(II) iodide in Example 1(2) and the compound obtained in Example 1(1) respectively, the title compound was obtained.

$^1$H-NMR(CDCl$_3$, 300 MHz) δ ppm: 0.86~1.86(m, 19H), 2.19~2.30(m, 1H), 2.24(dd, J=8.9 Hz, 18.5 Hz, 1H), 2.33~2.41(m, 2H), 2.66(ddd, J=1.8 Hz, 8.2 Hz, 11.2 Hz, 1H), 2.76(ddd, J=1.3 Hz, 7.3 Hz, 18.5 Hz, 1H), 3.76(s, 3H), 4.29~4.38(m, 1H), 4.49(dt, J=1.8 Hz, 6.4 Hz, 1H)

IR(neat): 3408, 2926, 2853, 2237, 1746, 1714, 1436, 1260, 1152, 1078, 1046, 754 cm$^{-1}$

EXAMPLE 14

(17RS)-20-Nor-17-methyl-19-(2'-methylprop-1'-enyl)-2,2,3,3,13,14-hexadehydro-PGE$_1$ Methyl Ester (Compound 7)

Following substantially similar manners to those of Examples 1(2) and (3) but using 5-carbomethoxypent-4-ynylzinc(II) iodide and the compound obtained Example 11(1) in place of (4E)-5-carbomethoxypent-4-enylzinc(II) iodide in Example 1(2) and the compound obtained in Example 1(1) respectively, the title compound was obtained.

$^1$H-NMR(CDCl$_3$, 300 MHz) δ ppm: 0.95(d, J=6.6 Hz, 3H), 1.14~2.10(m, 13H), 1.61(s, 3H), 1.68(s, 3H), 2.19~2.30(m, 1H), 2.24(dd, J=8.9 Hz, 18.5 Hz, 1H), 2.32~2.40(m, 2H), 2.66(ddd, J=1.6 Hz, 8.2 Hz, 11.2 Hz, 1H), 2.76(ddd, J=1.1 Hz, 7.3 Hz, 18.5 Hz, 1H), 3.76(s, 3H), 4.28~4.39(m, 1H), 4.43~4.53(m, 1H), 5.04~5.13(m, 1H)

IR(neat): 3401, 2920, 2864, 2237, 1746, 1718, 1436, 1379, 1259, 1153, 1078, 822, 754 cm$^{-1}$

EXAMPLE 15

(2E 16RS)-16-Methyl-2,3,13,14-tetradehydro-PGE$_1$ Methyl Ester (1) Following a substantially similar manner to that of Example 1(1) but using (3S,4RS)-3-(t-butyldimethylsiloxy)-4-methyloct-1-yne in place of (3S,5S)-3-(t-butyldimethylsiloxy)-5-methylnon-1-yne in Example 1(1), there was obtained (3R,4R)-2-methylene-3-[(3'S,4'RS)-3'-(t-butyldimethylsiloxy)-4'-methyloct-1'-ynyl]-4-(t-butyldimethylsiloxy)cyclopentan-1-one.

$^1$H-NMR(CDCl$_3$, 300 MHz) δ ppm: 0.03~0.17(m, 12H), 0.60~1.75(m, 31H), 2.33(dd, J=7.3 Hz, 17.9 Hz, 1H), 2.72(dd, J=6.4 Hz, 17.9 Hz, 1H), 3.48~3.58(m, 1H), 4.15~4.56(m, 1H), 5.56(d, J=3.0 Hz, 1H), 6.14(d, J=3.5 Hz, 1H)

IR(neat): 2957, 2931, 2858, 2231, 1738, 1644, 1464, 1362, 1255, 1083, 1006, 940, 838, 778, 671 cm$^{-1}$ (2) Following similar manners to those of Examples 1(2) and (3) using the compound obtained in the above item (1), the title compound was obtained.

$^1$H-NMR(CDCl$_3$, 300 MHz) δ ppm: 0.85~0.96(m, 3H), 0.99(d, J=6.7 Hz, 3H), 1.10~1.87(m, 13H), 2.17~2.30(m, 3H), 2.24(dd, J=9.1 Hz, 18.5 Hz, 1H), 2.64(ddd, J=1.7 Hz, 8.2 Hz, 9.9 Hz, 1H), 2.76(dd, J=7.3 Hz, 18.5 Hz, 1H), 3.73(s, 3H), 4.25~4.38(m, 2H), 5.83(d, J=15.7 Hz, 1H), 6.96(dt, J=7.0 Hz, 15.7 Hz, 1H)

IR(neat): 3420, 2931, 2860, 2236, 1746, 1728, 1657, 1438, 1275, 1203, 1158, 1079, 1036 cm$^{-1}$

EXAMPLE 16

(2E,15RS)-16,16-Dimethyl-2,3,13,14-tetradehydro-PGE$_1$ Methyl Ester (1) Following a substantially similar manner to that of Example 1(1) but using (3RS)-3-(t-butyldimethylsiloxy)-4,4-dimethyloct-1-yne in place of (3S,5S)-3-(t-butyldimethylsiloxy)-5-methylnon-1-yne in Example 1(1), there was obtained (3R,4R)-2-methylene-3-[(3'RS)-3'-(t-butyldimethylsiloxy)-4',4'-dimethyloct-1'-ynyl]-4-(t-butyldimethylsiloxy)cyclopentan-1-one.

$^1$H-NMR(CDCl$_3$, 300 MHz) δ ppm: 0.02~0.17(m, 12H), 0.73~1.64(m, 33H), 2.33(dd, J=7.0 Hz, 17.8 Hz, 1H), 2.72(dd, J=6.4 Hz, 17.8 Hz, 1H), 3.49~3.59(m, 1H), 4.02~4.07(m, 1H), 4.22~4.34(m, 1H), 5.53~5.58(m, 1H), 6.15(d, J=3.0 Hz, 1H)

IR(neat): 2957, 2931, 2212, 1738, 1714, 1621, 1472, 1387, 1363, 1256, 1083, 1007, 940, 838, 778, 671 cm$^{-1}$ (2) Following similar manners to those of Examples 1(2) and (3) using the compound obtained in the above item (1), the title compound was obtained.

$^1$H-NMR(CDCl$_3$, 300 MHz) δ ppm: 0.91(t, J=7.0 Hz, 3H), 0.94(s, 3H), 0.96(s, 3H), 1.19~1.87(m, 12H), 2.15~2.35 (m, 3H), 2.24(dd, J=9.2 Hz, 18.5 Hz, 1H), 2.65(ddd, J=1.8 Hz, 8.3 Hz, 11.4 Hz, 1H), 2.76(ddd, J=1.3 Hz, 7.3 Hz, 18.5 Hz, 1H), 3.73(s, 3H), 4.07~4.17(m, 1H), 4.27~4.40 (m, 1H), 5.82(dt, J=1.5 Hz, 15.6 Hz, 1H), 6.95(dt, J=7.0 Hz, 15.6 Hz, 1H)

IR(neat): 3435, 2932, 2861, 2233, 1746, 1728, 1657, 1438, 1385, 1275, 1202, 1159, 1079, 1034 cm −1

EXAMPLE 17

(2E,17S)-2a-Homo-17,20-dimethyl-2,2a,13,14-tetradehydro-PGE$_1$ Methyl Ester Following a substantially similar manner to that of Example 1 but using (5E)-6-carbomethoxyhex-5-enylzinc (II) iodide in place of (4E)-5-carbomethoxypent-4-enylzinc (II) iodide in Example 1(2), the title compound was obtained.

$^1$H-NMR(CDCl$_3$, 300 MHz) δ ppm: 0.86~0.95(m, 6H), 1.10~1.83(m, 17H), 2.16~2.29(m, 3H), 2.23(dd, J=9.0 Hz, 18.5 Hz, 1H), 2.64(ddd, J=1.7 Hz, 8.2 Hz, 11.3 Hz, 1H), 2.76(ddd, J=1.3 Hz, 7.2 Hz, 18.5 Hz, 1H), 3.73(s, 3H), 4.28~4.38(m, 1H), 4.48(dt, J=1.7 Hz, 7.1 Hz, 1H), 5.82(dt, J=1.5 Hz, 15.7 Hz, 1H), 6.96(dt, J=7.0 Hz, 15.7 Hz, 1H)

IR(neat): 3419, 2930, 2858, 2237, 1747, 1729, 1658, 1462, 1438, 1319, 1276, 1201, 1162, 1078, 1044, 853, 727 cm$^{-1}$

EXAMPLE 18

(2E,17S)-2a,2b-Dihomo-17,20-dimethyl-2,2a,13,14-tetradehydro-PGE$_1$ Methyl Ester Following a substantially similar manner to that of Example 1 but using (6E)-7-carbomethoxyhept-6-enylzinc (II) iodide in place of (4E)-5-carbomethoxypent-4-enylzinc (II) iodide in Example 1(2), the title compound was obtained.

$^1$H-NMR(CDCl$_3$, 300 MHz) δ ppm: 0.85~0.96(m, 6H), 1.06~1.86(m, 19H), 2.15~2.27(m, 3H), 2.23(dd, J=9.2 Hz, 18.5 Hz, 1H), 2.65(ddd, J=1.7 Hz, 8.3 Hz, 11.5 Hz, 1H), 2.75(ddd, J=1.2 Hz, 7.2 Hz, 18.5 Hz, 1H), 3.73(s, 3H), 4.28~4.38(m, 1H), 4.47(dt, J=1.7 Hz, 7.1 Hz, 1H), 5.82(dt, J=1.5 Hz, 15.6 Hz, 1H), 6.96(dt, J=7.0 Hz, 15.6 Hz, 1H)

IR(neat): 3413, 2929, 2858, 2236, 1746, 1728, 1657, 1438, 1273, 1201, 1172, 1044, 984 cm$^{-1}$

EXAMPLE 19

(17S)-2-Nor-17,20-dimethyl-3,3,4,4,13,14-hexadehydro-PGE$_1$ Methyl Ester

Following a substantially similar manner to that of Example 1 but using 4-carbomethoxybut-3-ynylzinc(II) iodide in place of (4E)-5-carbomethoxypent- 4-enylzinc(II) iodide in Example 1(2), the title compound was obtained.

$^1$H-NMR(CDCl$_3$, 300 MHz) δ ppm: 0.86~0.95(m, 6H), 1.10~1.95(m, 13H), 2.05(d, J=5.8 Hz, 1H), 2.22~2.31(m, 1H), 2.25(dd, J=8.8 Hz, 18.6 Hz, 1H), 2.38(t, J=6.9 Hz, 2H), 2.45(d, J=3.4 Hz, 1H), 2.66(ddd, J=1.7 Hz, 8.1 Hz, 11.2 Hz, 1H), 2.77(ddd, J=1.3 Hz, 7.3 Hz, 18.6 Hz, 1H), 3.76(s, 3H), 4.30~4.40(m, 1H), 4.43~4.52(m, 1H)

IR(neat): 3402, 2955, 2929, 2872, 2238, 1747, 1717, 1436, 1379, 1260, 1153, 1077, 754 cm$^{-1}$

EXAMPLE 20

(17S)-2a-Homo-17,20-dimethyl-2,2,2a,2a,13,14-hexadehydro-PGE$_1$ Methyl Ester Following a substantially similar manner to that of Example 1 but using 6-carbomethoxyhex-5-ynylzinc(II) iodide in place of (4E)-5-carbomethoxypent-4-enylzinc(II) iodide in Example 1(2), the title compound was obtained.

$^1$H-NMR(CDCl$_3$, 300 MHz) δ ppm: 0.85~0.96(m, 6H), 1.12~1.86(m, 17H), 2.24(dd, J=9.7 Hz, 18.5 Hz, 1H), 2.20~2.30(m, 1H), 2.34(t, J=6.9 Hz, 2H), 2.65(ddd, J=1.7 Hz, 8.3 Hz, 11.2 Hz, 1H), 2.76(ddd, J=1.3 Hz, 7.1 Hz, 18.5 Hz, 1H), 3.76(s, 3H), 4.27~4.38(m, 1H), 4.48(dt, J=1.7 Hz, 7.1 Hz, 1H)

IR(neat): 3408, 2931, 2860, 2238, 1747, 1717, 1461, 1436, 1328, 1259, 1157, 1078, 754 cm$^{-1}$

EXAMPLE 21

(2E,17R)-17,20-Dimethyl-2,3,13,14-tetradehydro-PGE$_1$ Allyl Ester

Following substantially similar manners to those of Examples 1(2) and 1(3) but using (4E)-5-carbo-[(prop-2'-enyl)oxy]pent-4-enylzinc(II) iodide and the compound obtained in Example 8(1) in place of (4E)-5-carbomethoxypent-4-enylzinc (II) iodide in Example 1(2) and the compound obtained in Example 1(1) respectively, the title compound was obtained.

$^1$H-NMR(CDCl$_3$, 300 MHz) δ ppm: 0.89(t, J=6.3 Hz, 3H), 0.93(d, J=6.6 Hz, 3H), 1.12~1.86(m, 15H), 2.15~2.31(m, 3H), 2.23(dd, J=9.2 Hz, 18.4 Hz, 1H), 2.63(ddd, J=1.8 Hz, 8.3 Hz, 11.3 Hz, 1H), 2.76(ddd, J=1.3 Hz, 7.3 Hz, 18.4 Hz, 1H), 4.27~4.38(m, 1H), 4.43~4.51(m, 1H), 4.64(ddd, J=1.4 Hz, 1.4 Hz, 5.7 Hz, 1H), 5.24(ddt, J=1.4 Hz, 1.4 Hz, 10.4 Hz, 1H), 5.33(ddt, J=1.4 Hz, 1.4 Hz, 17.2 Hz, 1H), 5.86(dt, J=1.5 Hz, 15.6 Hz, 1H), 5.95(ddt, J=5.7 Hz, 10.4 Hz, 17.2 Hz, 1H), 6.99(dt, J=7.0 Hz, 15.6 Hz, 1H)

IR(neat): 3412, 2930, 2859, 2236, 1747, 1724, 1652, 1461, 1383, 1274, 1176, 1030, 991, 935, 729 cm$^{-1}$

EXAMPLE 22

(17R)-17,20-Dimethyl-2,2,3,3,13,14-hexadehydro-PGE$_1$ Methyl Ester (Compound 8)

Following substantially similar manners to those of Examples 1(2) and (3) using 5-carbomethoxypent-4- ynylzinc(II) iodide and the compound obtained in Example 8(1) in place of (4E)-5-carbomethoxypent-4-enylzinc(II) iodide in Example 1(2) and the compound obtained in Example 1(1) respectively, the title compound was obtained.

$^1$H-NMR(CDCl$_3$, 300 MHz) δ ppm: 0.90(t, J=6.4 Hz, 3H), 0.93(d, J=6.6 Hz, 3H), 1.12~1.86(m, 15H), 2.08(d, J=5.9 Hz, 1H), 2.18~2.29(m, 1H), 2.24(dd, J=8.9 Hz, 18.6 Hz, 1H), 2.32~2.41(m, 2H), 2.51(d, J=3.4 Hz, 1H), 2.06(ddd, J=1.8 Hz, 8.1 Hz, 11.2 Hz, 1H), 2.77(ddd, J=1.3 Hz, 7.2 Hz, 18.6 Hz, 1H), 3.77(s, 3H), 4.28~4.39(m, 1H), 4.43~4.52(m, 1H)

IR(neat): 3412, 2930, 2861, 2237, 1747, 1715, 1436, 1384, 1260, 1153, 1078, 821, 754 cm$^{-1}$

EXAMPLE 23

(2E,17S)-17,20-Dimethyl-2,3,13,14-tetradehydro-PGE$_1$ (Compound 9)

To a solution of 500 mg of lipase VII in 22.5 ml of phosphate buffer (10 mM, pH 7.0) was added a solution of 50 mg (0.127 mmol) of (2E,17S)-17,20-dimethyl- 2,3,13, 14-tetradehydro-PGE$_1$ methyl ester (obtained in Example 1) in 2.5 ml of 50% (v/v) acetone-water, followed by stirring at 30° C. for 5 hours. The reaction solution was extracted 3 times with 30 ml of ethyl acetate, and the organic layer was washed with 30 ml of a saturated aqueous sodium chloride solution, dried over anhydrous magnesium sulfate and concentrated. The resulting crude product was purified by silica gel column chromatography (eluent; ethyl acetate:methanol=40:1) to give 41 mg of the title compound.

$^1$H-NMR(CDCl$_3$, 300 MHz) δ ppm: 0.86~0.94(m, 3H), 0.91(d, J=6.3 Hz, 3H), 1.10~1.88(m, 15H), 2.18~2.35(m, 3H), 2.24(dd, J=8.8 Hz, 18.6 Hz, 1H), 2.64(ddd, J=1.7 Hz, 8.1 Hz, 11.2 Hz, 1H), 2.76(ddd, J=1.2 Hz, 7.3 Hz, 18.6 Hz, 1H), 4.28~4.38(m, 1H), 4.47(dt, J=1.7 Hz, 7.1 Hz, 1H), 5.84(dt, J=1.5 Hz, 15.6 Hz, 1H), 7.06(dt, J=7.1 Hz, 15.6 Hz, 1H)

IR(neat): 3391, 2930, 2859, 2239, 1741, 1698, 1654, 1461, 1381, 1285, 1164, 1076, 984, 757 cm$^{-1}$

EXAMPLE 24–39

The compounds prepared in the following Examples 24 to 39 are those obtained by following a similar hydrolysis to that of Example 23 using the corresponding materials obtained in Examples 1–22.

EXAMPLE 24

(2E,16RS)-16,20-Dimethyl-2,3,13,14,18,18,19,19-octadehydro-PGE$_1$ (Compound 10)

$^1$H-NMR(CDCl$_3$, 300 MHz) δ ppm: 0.90~1.32(m, 6H), 1.35~2.01(m, 7H), 2.04~2.50(m, 8H), 2.63(t, J=10.0 Hz, 1H), 2.75(dd, J=7.2 Hz, 18.5 Hz, 1H), 4.27~4.37(m, 1H), 4.41 and 4.45(2d, J=6.5 Hz and J=4.5 Hz, 1H), 5.82(d, J=15.7 Hz, 1H), 7.04(dt, J=15.7 Hz, 7.3 Hz, 1H)

EXAMPLE 25

(2E)-16,17,18,19,20-Pentanor-15-cyclohexyl-2,3,13, 14-tetradehydro-PGE$_1$ (Compound 11)

$^1$H-NMR(CDCl$_3$, 300 MHz) δ ppm: 0.83~1.98(m, 17H), 2.12~2.42(m, 4H), 2.63(t, J=9.3 Hz, 1H), 2.75(dd, J=7.7 Hz, 18.7 Hz, 1H), 4.17(d, J=6.1 Hz, 1H), 4.27~4.37(m, 1H), 5.82(d, J=15.6 Hz, 1H), 7.04(dt, J=15.6 Hz, 6.5 Hz, 1H)

EXAMPLE 26

(16RS)-16,20-Dimethyl-2,2,3,3,13,14,18,18,19,19-decadehydro-PGE$_1$ $^1$H-NMR(CDCl$_3$, 300 MHz) δ ppm: 1.05(d, J=6.7 Hz, 3H), 1.11(t, J=7.5 Hz, 3H), 1.79~1.90(m, 1H), 2.01~2.88(m, 15H), 3.10(q, J=7.6 Hz, 1H), 3.71(s, 3H), 4.24~4.33(m, 1H), 4.32 and 4.38(2d, J=4.1 Hz and J=2.9 Hz, 1H), 6.51(br. s, 3H)

EXAMPLE 27

(17S)-17,20-Dimethyl-2,2,3,3,13,14-hexadehydro-PGE$_1$ (Compound 12)

$^1$H-NMR(CDCl$_3$, 300 MHz) δ ppm: 0.80~0.92(m, 6H), 1.02~1.88(m, 15H), 2.20~2.46(m, 2H), 2.37(t, J=6.0 Hz, 2H), 2.59~2.66(m, 1H), 2.75(dd, J=7.4 Hz, 18.5 Hz, 1H), 4.28~4.42(m, 1H), 4.46(t, J=6.4 Hz, 1H)

IR(neat): 3370, 2930, 2240, 1700, 1370, 1240, 1040, 730 cm$^{-1}$

EXAMPLE 28

(2E,17RS)-17-Methyl-20-ethyl-2,3,13,14-tetradehydro-PGE$_1$ (Compound 13)

$^1$H-NMR(CDCl$_3$, 300 MHz) δ ppm: 0.73~1.01(m, 6H), 1.01~1.89(m, 17H), 2.11~2.38(m, 4H), 2.52~2.82(m, 1H), 2.75(dd, J=7.1 Hz, 18.4 Hz, 1H), 4.22~4.49(m, 2H), 5.83(d, J=15.5 Hz, 1H), 7.04(dt, J=7.4 Hz, 15.5 Hz, 1H)

IR(neat): 3350, 2920, 2860, 2320, 1700, 1650, 1380, 1280, 1160, 980 cm$^{-1}$

EXAMPLE 29

(2E,17R)-17,20-Dimethyl-2,3,13,14-tetradehydro-PGE$_1$ (Compound 14)

$^1$H-NMR(CDCl$_3$, 300 MHz) δ ppm: 0.86~0.95(m, 3H), 0.93(d, J=6.6 Hz, 3H), 1.09~1.86(m, 15H), 2.18~2.31(m, 3H), 2.24(dd, J=9.1 Hz, 18.5 Hz, 1H), 2.64(ddd, J=1.7 Hz, 8.3 Hz, 11.4 Hz, 1H), 2.76(ddd, J=1.3 Hz, 7.3 Hz, 18.5 Hz, 1H), 4.27~4.37(m, 1H), 4.43~4.51(m, 1H), 5.84(dt, J=1.4 Hz, 15.6 Hz, 1H), 7.60(dt, J=7.0 Hz, 15.6 Hz, 1H)

IR(neat): 3368, 2930, 2860, 2238, 1745, 1697, 1653, 1462, 1383, 1285, 1158, 1071, 984, 758, 668 cm$^{-1}$

EXAMPLE 30

(2E)-17,18,19,20-Tetranor-16-cyclohexyl-2,3,13,14-tetradehydro-PGE$_1$ $^1$H-NMR(CDCl$_3$, 300 MHz) δ ppm: 0.82~1.82(m, 19H), 2.12~2.37(m, 4H), 2.54~2.69(m, 1H), 2.77(dd, J=7.4 Hz, 18.6 Hz, 1H), 4.25~4.52(m, 2H), 5.84(d, J=15.4 Hz, 1H), 7.05(dt, J=7.0 Hz, 15.4 Hz, 1H)

IR(neat): 3380, 2900, 2850, 2315, 1690, 1400, 1270, 1160, 1020, 975 cm$^{-1}$

EXAMPLE 31

(2E)-17,18,19,20-Tetranor-16-cyclopentyl-2,3,13,14-tetradehydro-PGE$_1$ $^1$H-NMR(CDCl$_3$, 300 MHz) δ ppm: 1.01~2.08(m, 17H), 2.13~2.31(m, 4H), 2.52~2.67(m, 1H), 2.76(dd, J=7.2 Hz, 18.5 Hz, 1H), 4.27~4.47(m, 1H), 4.41(t, J=7.0 Hz, 1H), 5.84(d, J=15.7 Hz, 1H), 7.05(dt, J=7.1 Hz, 15.7 Hz, 1H)

IR(neat): 3380, 2920, 2850, 2320, 1690, 1645, 1400, 1280, 1150, 1075, 1035, 980 cm$^{-1}$

EXAMPLE 32

(2E,17RS)-20-Nor-17-methyl-19-(2'-methylprop-1'-enyl)-2,3,13,14-tetradehydro-PGE$_1$ $^1$H-NMR(CDCl$_3$, 300 MHz) δ ppm: 0.82~1.00(m, 3H), 1.06~2.35(m, 16H), 1.59(s, 3H), 1.67(s, 3H), 2.58~2.67 (m, 2H), 2.75(dd, J=7.2 Hz, 18.6 Hz, 1H), 4.26~4.49(m, 2H), 5.00~5.12(m, 1H), 5.83(d, J=15.5 Hz, 1H), 7.04(dt, J=7.1 Hz, 15.5 Hz, 1H)

EXAMPLE 33

(2E,16RS)-16-Methyl-2,3,13,14-tetradehydro-PGE$_1$ $^1$H-NMR(CDCl$_3$, 300 MHz) δ ppm: 0.84~0.96(m, 3H), 0.99(d, J=6.7 Hz, 3H), 1.10~1.90(m, 13H), 2.16~2.36(m, 3H), 2.24(dd, J=9.0 Hz, 18.6 Hz, 1H), 2.65(ddd, J=1.8 Hz, 8.3 Hz, 11.4 Hz, 1H), 2.76(ddd, J=1.3 Hz, 7.3 Hz, 18.6 Hz, 1H), 4.27~4.39(m, 2H), 5.84(dt, J=1.5 Hz, 15.6 Hz, 1H), 7.05(dt, J=7.0 Hz, 15.6 Hz, 1H)
IR(neat): 3391, 2931, 2860, 2237, 1744, 1698, 1653, 1462, 1418, 1378, 1284, 1158, 1078, 1032, 758 cm$^{-1}$

EXAMPLE 34

(2E,15RS)-16,16-Dimethyl-2,3,13,14-tetradehydro-PGE$_1$ $^1$H-NMR(CDCl$_3$, 300 MHz) δ ppm: 0.91(t, J=6.9 Hz, 3H), 0.94(s, 3H), 0.96(s, 3H), 1.15~1.87(m, 12H), 2.20~2.32 (m, 3H), 2.23(dd, J=9.1 Hz, 18.5 Hz, 1H), 2.66(ddd, J=1.7 Hz, 8.2 Hz, 11.4 Hz, 1H), 2.77(ddd, J=1.2 Hz, 7.3 Hz, 18.5 Hz, 1H), 4.08~4.17(m, 1H), 4.29~4.39(m, 1H), 5.84 (dt, J=1.5 Hz, 15.6 Hz, 1H), 7.05(dt, J=7.0 Hz, 15.6 Hz, 1H)
IR(neat): 3392, 2932, 2861, 2235, 1743, 1697, 1653, 1385, 1284, 1159, 1077, 1024 cm$^{-1}$

EXAMPLE 35

(2E,17S)-2a-Homo-17,20-dimethyl-2,2a,13,14-tetradehydro-PGE$_1$ $^1$H-NMR(CDCl$_3$, 300 MHz) δ ppm: 0.85~0.97(m, 6H), 1.10~1.87(m, 17H), 2.17~2.30(m, 3H), 2.24(dd, J=9.2 Hz, 18.5 Hz, 1H), 2.64(ddd, J=1.7 Hz, 8.3 Hz, 11.3 Hz, 1H), 2.76(ddd, J=1.2 Hz, 7.2 Hz, 18.5 Hz, 1H), 4.28~4.38 (m, 1H), 4.48(dt, J=1.7 Hz, 7.4 Hz, 1H), 5.83(dt, J=1.4 Hz, 15.6 Hz, 1H), 7.06(dt, J=7.0 Hz, 15.6 Hz, 1H)
IR(neat): 3369, 2929, 2858, 2237, 1744, 1697, 1654, 1384, 1284, 1160, 1075, 983 cm$^{-1}$

EXAMPLE 36

(2E,17S)-2a,2b-Dihomo-17,20-dimethyl-2,2a,13,14-tetradehydro-PGE$_1$ (Compound 15)

$^1$H-NMR(CDCl$_3$, 300 MHz) δ ppm: 0.84~0.95(m, 6H), 1.12~1.84(m, 19H), 2.17~2.30(m, 3H), 2.23(dd, J=9.2 Hz, 18.4 Hz, 1H), 2.65(ddd, J=1.7 Hz, 8.3 Hz, 11.5 Hz, 1H), 2.76(ddd, J=1.2 Hz, 7.2 Hz, 18.4 Hz, 1H), 4.28~4.38 (m, 1H), 4.47(dt, J=1.7 Hz, 7.1 Hz, 1H), 5.83(dt, J=1.4 Hz, 15.6 Hz, 1H), 7.06(dt, J=7.0 Hz, 15.6 Hz, 1H)
IR(neat): 3382, 2928, 2858, 2237, 1746, 1697, 1653, 1465, 1418, 1379, 1284, 1162, 1076, 1046, 984 cm$^{-1}$

EXAMPLE 37

(17S)-2-Nor-17,20-dimethyl-3,3,4,4,13,14-hexadehydro-PGE$_1$ $^1$H-NMR(CDCl$_3$, 300 MHz) δ ppm: 0.86~0.95(m, 6H), 1.10~1.96(m, 13H), 2.21~2.34(m, 1H), 2.26(dd, J=8.8 Hz, 18.7 Hz, 1H), 2.40(t, J=6.4 Hz, 2H), 2.68(ddd, J=1.5 Hz, 8.3 Hz, 11.3 Hz, 1H), 2.78(ddd, J=1.1 Hz, 7.3 Hz, 18.7 Hz, 1H), 4.30~4.41(m, 1H), 4.42~4.54(m, 1H)
IR(neat): 3392, 2956, 2929, 2872, 2237, 1739, 1698, 1458, 1383, 1266, 1154, 1070, 757 cm$^{-1}$

EXAMPLE 38

(17S)-2a-Homo-17,20-dimethyl-2,2,2a,2a,13,14-hexadehydro-PGE$_1$ $^1$H-NMR(CDCl$_3$, 300 MHz) δ ppm: 0.85~0.96(m, 6H), 1.12~1.88(m, 17H), 2.19~2.33(m, 1H), 2.25(dd, J=8.9 Hz, 18.5 Hz, 1H), 2.37(t, J=6.9 Hz, 2H), 2.67(ddd, J=1.7 Hz, 8.3 Hz, 11.2 Hz, 1H), 2.77(ddd, J=1.3 Hz, 7.1 Hz, 18.5 Hz, 1H), 4.29~4.39(m, 1H), 4.50(dt, J=1.7 Hz, 7.6 Hz, 1H)
IR(neat): 3392, 2930, 2860, 2236, 1707, 1462, 1384, 1241, 1073, 757 cm$^{-1}$

EXAMPLE 39

(17R)-17,20-Dimethyl-2,2,3,3,13,14-hexadehydro-PGE$_1$ (Compound 16)

$^1$H-NMR(CDCl$_3$, 300 MHz) δ ppm: 0.82~0.96(m, 3H), 0.93(d, J=6.6 Hz, 3H), 1.10~1.88(m, 15H), 2.22~2.32(m, 1H), 2.26(dd, J=9.0 Hz, 18.6 Hz, 1H), 2.37~2.44(m, 2H), 2.68(ddd, J=1.7 Hz, 8.2 Hz, 11.3 Hz, 1H), 2.78(ddd, J=1.2 Hz, 7.4 Hz, 18.6 Hz, 1H), 4.29~4.39(m, 1H), 4.45~4.52 (m, 1H)
IR(neat): 3391, 2930, 2861, 2237, 1740, 1697, 1462, 1384, 1259, 1154, 1071, 757 cm$^{-1}$

EXAMPLE 40

(2E,17R)-17,20-Dimethyl-2,3,13,14-tetradehydro-PGE$_1$ (Compound 14)

(1) A solution of copper (I) cyanide-dilithium dichloride (2.37 g, 13.6 mmol) in tetrahydrofuran (13.6 ml) was added at −70° C. to (4E)-5-carbo[(prop-2'-enyl)oxy]pent-4-enylzinc(II) iodide (0.81M tetrahydrofuran solution, 13.5 ml, 10.9 mmol), followed by stirring at the same temperature for 15 minutes. To the solution were added at −70° C., (3R,4R)-2-methylene-3-[(3'S,5'R)-3'-(t-butyldimethylsiloxy)-5'-methylnon-1'-ynyl]-4-(t-butyldimethylsiloxy)cyclopentan-1-one (2.69 g, 5.45 mmol) obtained in Example 8(1) and a solution of trimethylsilyl chloride (1.25 ml, 9.81 mmol) in diethyl ether, followed by stirring to raise the temperature to room temperature over about a 2 hour period. The reaction solution, after addition of a saturated aqueous ammonium chloride solution (80 ml), was extracted with n-hexane. The organic layer was washed with a saturated aqueous sodium chloride solution, dried and concentrated. The resulting residue was dissolved in ether-isopropyl alcohol (1:4, 22 ml) and then pyridinium p-toluenesulfonate (68 mg, 0.27 mmol) was added thereto, followed by stirring at room temperature for 12 hours. After addition of ether (50 ml) and a saturated aqueous sodium bicarbonate solution (20 ml), the reaction solution was extracted, and the organic layer was dried and concentrated.

The resulting residue was chromatographed on silica gel column (n-hexane:ether=4:1) to give 2.52 g of (2E,17R)-17,20-dimethyl-2,3,13,14-tetradehydro-PGE$_1$ allyl ester 11,15-bis(t-butyldimethylsilyl ether).

$^1$H-NMR(CDCl$_3$, 300 MHz) δ ppm: 0.09, 0.11 and 0.12(3s, 12H), 0.71~1.00(m, 6H), 0.87 and 0.89(2s, 18H), 1.00~1.80(m, 15H), 2.08~2.29(m, 4H), 2.60~2.73(m, 2H), 4.22~4.32(m, 1H), 4.34~4.48(m, 1H), 4.63(d, J=5.7 Hz, 2H), 5.19~5.37(m, 2H), 5.84(d, J=15.5 Hz, 1H), 5.83~6.01(m, 1H), 6.98(dt, J=15.5 Hz, 7.0 Hz, 1H)

IR(neat): 2955, 2930, 2858, 2235, 1749, 1726, 1655, 1463, 1380, 1362, 1256, 1124, 1089, 991, 838, 778, 669 cm$^{-1}$ (2) Tetrakis(triphenylphosphine)palladium(0) (34.7 mg, 0.030 mmol) was added to a solution of the compound (194 mg, 0.30 mmol) obtained in the above item (1) in tetrahydrofuran (3.0 ml), followed by stirring at room temperature for 10 minutes. To this was added morpholine (0.130 ml, 1.50 mmol), followed by stirring at room temperature for 20 minutes. After addition of a saturated aqueous sodium chloride solution (10 ml), the mixture was extracted with n-hexane (15 ml), and the organic layer was dried and concentrated. The resulting residue was chromatographed on silica gel column (n-hexane:ether=9:1) to give 135 mg of (2E,17R)-17,20-dimethyl-2,3,13,14-tetradehydro-PGE$_1$ 11,15-bis(t-butyldimethylsilyl ether).

$^1$H-NMR(CDCl$_3$, 300 MHz) δ ppm: 0.10, 0.11 and 0.13(3s, 12H), 0.76~1.00(m, 6H), 0.87 and 0.89(2s, 18H), 1.00~1.92(m, 15H), 2.09~2.31(m, 4H), 2.59~2.72(m, 2H), 4.21~4.34(m, 1H), 4.36~4.46(m, 1H), 5.82(d, J=15.7 Hz, 1H), 7.06(dt, J=6.9 Hz, 15.7 Hz, 1H)

IR(neat): 2955, 2930, 2858, 2236, 1749, 1698, 1652, 1464, 1421, 1382, 1362, 1286, 1253, 1123, 1089, 985, 940, 838, 778, 670 cm$^{-1}$ (3) A 50% aqueous hydrofluoric acid solution (12.2 ml) was added at 0° C. to a solution of the compound (920 mg, 1.52 mmol) obtained in the above item (2) in acetonitrile (51 ml), followed by stirring at 0° C. for 90 minutes. The reaction solution was poured into ethyl acetate (100 ml)—a saturated aqueous sodium bicarbonate solution (350 ml), extracted with ethyl acetate, washed with a saturated aqueous sodium chloride solution and concentrated. The resulting residue was purified by silica gel column chromatography (ether:ethyl acetate=1:1) to give 568 mg of the title compound (identical to the compound of Example 29).

EXAMPLE 41

(2Z,17S)-17,20-Dimethyl-2,3,13,14-tetradehydro-PGE$_1$ Methyl Ester (1) Following substantially similar manners to those of Examples 1(1) and (2) but using 5-carbomethoxypent-4-ynylzinc(II) iodide in place of (4E)-5-carbomethoxypent-4-enylzinc(II) iodide in Example 1(2), there was obtained (17S)-17,20-dimethyl-2,2,3,3,13,14-hexadehydro-PGE$_1$ methyl ester 11,15-bis(t-butyldimethylsilyl ether).

$^1$H-NMR(CDCl$_3$, 300 MHz) δ ppm: 0.10(s, 6H), 0.11(s, 3H), 0.13(s, 3H), 0.83~1.00(m, 6H), 0.89(s, 9H), 0.90(s, 9H), 1.05~1.85(m, 15H), 2.13~2.27(m, 1H), 2.17(dd, J=6.8 Hz, 18.3 Hz, 1H), 2.34(t, J=6.5 Hz, 2H), 2.58~2.76 (m, 2H), 3.75(s, 3H), 4.23~4.36(m, 1H), 4.43(dt, J=1.4 Hz, 6.9 Hz, 1H)

IR(neat): 2954, 2930, 2858, 2239, 1749, 1719, 1463, 1435, 1256, 1079, 837, 779 cm$^{-1}$ (2) A mixture of formic acid (0.29 ml, 6.65 mmol), triethylamine (0.79 ml, 5.69 mmol), tris(dibenzylideneacetone)dipalladium(0)-chloroform complex (51.8 mg, 0.05 mmol) and tributylphosphine (47 ml, 0.19 mmol) was stirred at room temperature for 10 minutes, and then tetrahydrofuran (9.7 ml) was added thereto, followed by stirring at room temperature for 15 minutes. A solution of the compound (1.18 g, 1.90 mmol) obtained in the item (1) in tetrahydrofuran (9.7 ml) was added thereto, followed by stirring at 50° C. for 30 minutes. To the mixture cooled to room temperature was added a saturated aqueous sodium chloride solution (20 ml), followed by extraction with n-hexane (20 ml). The organic layer was dried and concentrated to give a residue, which was then chromatographed on silica gel column (n-hexane:ether=2:1) to give 405 mg of the title compound.

$^1$H-NMR(CDCl$_3$, 300 MHz) δ ppm: 0.83~0.98(m, 6H), 1.09~1.90(m, 15H), 2.10~2.36(m, 4H), 2.56~2.68(m, 1H), 2.75(dd, J=7.3 Hz, 18.4 Hz, 1H), 3.72(s, 3H), 4.20~4.38(m, 1H), 4.47(t, J=5.7 Hz, 1H), 5.79(d, J=11.5 Hz, 1H), 6.31(dt, J=7.5 Hz, 11.5 Hz, 1H)

IR(neat): 3413, 2930, 2859, 2235, 1746, 1728, 1649, 1462, 1438, 1319, 1276, 1162, 1042 cm$^{-1}$

EXAMPLE 42

(2Z)-17,18,19,20-Tetranor-16-cyclopentyl-2,3,13,14-tetradehydro-PGE$_1$ (1) Following substantially similar manners to those of Examples 1(1) and (2) using (3S)-3-(t-butyldimethylsiloxy)-3-cyclopentylprop-1-yne and (4E)-5carbo-[(prop-2'-enyl)oxy]pent-4-enylzinc(II) iodide in place of (3S,5S)-3-(t-butyldimethylsiloxy)-5-methylnon-1-yne in Example 1(1) and (4E)-5-carbomethoxypent-4-enylzinc(II) iodide in Example 1(2), there was obtained 17,18,19,20-tetranor-16-cyclopentyl-2,2,3,3,13,14-hexadehydro-PGE$_1$ allyl ester 11,15-bis(t-butyldimethylsilyl ether).

$^1$H-NMR(CDCl$_3$, 300 MHz) δ ppm: 0.09, 0.11 and 0.12(3s, 12H), 0.89(s, 18H), 1.01~1.85(m, 17H), 1.86~2.11(m, 1H), 2.17(dd, J=7.1 Hz, 18.3 Hz, 1H), 2.34(t, J=6.6 Hz, 2H), 2.61~2.67(m, 2H), 4.25~4.41(m, 2H), 4.64(d, J=5.8 Hz, 2H), 5.22~5.45(m, 2H), 5.93(ddt, J=5.8 Hz, 10.4 Hz, 17.0 Hz, 1H)

(2) Following a substantially similar manner to that of Example 41(2) using the compound obtained in the item (1), the title compound was obtained.

$^1$H-NMR(CDCl$_3$, 300 MHz) δ ppm: 1.00~2.03(m, 17H), 2.07~2.30(m, 2H), 2.52~2.74(m, 4H), 4.22~4.41(m, 2H), 5.78(d, J=11.4 Hz, 1H), 6.30(dt, J=7.5 Hz, 11.4 Hz, 1H)

We claim:

1. A prostaglandin PGE$_1$ analogue represented by the formula:

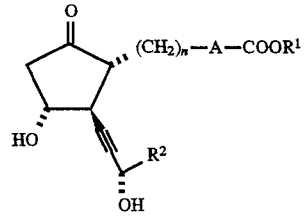

(wherein A is a vinylene group or an ethynylene group, R$^1$ is a hydrogen atom, an alkyl group having 1 to 6 carbon atoms or an allyl group, R$^2$ is a branched aliphatic hydrocarbon group having 5 to 10 carbon atoms, and n is an integer of 3 to 6), or a salt thereof.

2. A compound represented by the formula:

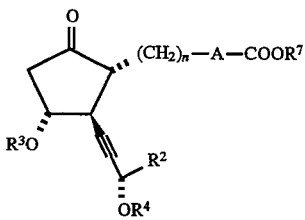

(wherein A is a vinylene group or an ethynylene group, $R^7$ is an alkyl group having 1 to 6 carbon atoms or an allyl group, $R^2$ is a hydrocarbon group having 5 to 10 carbon atoms, $R^3$ and $R^4$ are the same or different, and are each a hydroxyl protecting group, and n is an integer of 3 to 6).

3. A $PGE_1$ analogue in accordance with claim 1 wherein $R^2$ is a branched chain alkyl group having 5 to 10 carbon atoms.

4. A $PGE_1$ analogue in accordance with claim 1 wherein $R^2$ is a cycloalkyl group having 5 to 10 carbon atoms.

5. A $PGE_1$ analogue in accordance with claim 1 wherein $R^2$ is an alkyl group of 1 to 2 carbon atoms substituted by a cycloalkyl group.

6. A $PGE_1$ analogue in accordance with claim 1 wherein $R^2$ is a branched chain alkenyl group having 5 to 10 carbon atoms.

7. A $PGE_1$ analogue in accordance with claim 1 wherein $R^2$ is a branched chain alkynyl group having 5 to 10 carbon atoms.

8. A $PGE_1$ analogue in accordance with claim 1 wherein A is vinylene.

9. A $PGE_1$ analogue in accordance with claim 1 wherein A is ethynylene.

10. A $PGE_1$ analogue in accordance with claim 2 wherein A is vinylene.

11. A $PGE_1$ analogue in accordance with claim 2 wherein A is ethynylene.

12. A $PGE_1$ analogue in accordance with claim 2 wherein $R^2$ is a branched chain alkyl group having 5 to 10 carbon atoms.

13. A $PGE_1$ analogue in accordance with claim 2 wherein $R^2$ is a cycloalkyl group having 5 to 10 carbon atoms.

14. A $PGE_1$ analogue in accordance with claim 2 wherein $R^2$ is an alkyl group of 1 to 2 carbon atoms substituted by a cycloalkyl group.

15. A $PGE_1$ analogue in accordance with claim 2 wherein $R^2$ is a branched chain alkenyl group having 5 to 10 carbon atoms.

16. A $PGE_1$ analogue in accordance with claim 2 wherein $R^2$ is a branched chain alkynyl group having 5 to 10 carbon atoms.

* * * * *

UNITED STATES PATENT AND TRADEMARK OFFICE
CERTIFICATE OF CORRECTION

PATENT NO. : 5,639,899
DATED : June 17, 1997
INVENTOR(S) : SATO et al

It is certified that error appears in the above-indentified patent and that said Letters Patent is hereby corrected as shown below:

Col. 5, lines 20-25, "  "

should read -- 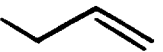 --.

Col. 18, line 64, "(71S)" should read --(17S)--.

Col. 20, line 26, "MH a)" should read -- MHz) --.

Signed and Sealed this

Eighteenth Day of August, 1998

Attest:

BRUCE LEHMAN

*Attesting Officer*   *Commissioner of Patents and Trademarks*